(12) United States Patent
Redko et al.

(10) Patent No.: US 11,851,778 B2
(45) Date of Patent: Dec. 26, 2023

(54) ELECTROCHEMICAL REDUCTIVE CARBOXYLATION OF UNSATURATED ORGANIC SUBSTRATES IN IONICALLY CONDUCTIVE MEDIUMS

(71) Applicant: BOARD OF TRUSTEES OF MICHIGAN STATE UNIVERSITY, East Lansing, MI (US)

(72) Inventors: Mikhail Redko, East Lansing, MI (US); Christopher M. Saffron, Okemos, MI (US); James E. Jackson, Haslett, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 118 days.

(21) Appl. No.: 16/634,192

(22) PCT Filed: Jul. 27, 2018

(86) PCT No.: PCT/US2018/044014
§ 371 (c)(1),
(2) Date: Jan. 27, 2020

(87) PCT Pub. No.: WO2019/023532
PCT Pub. Date: Jan. 31, 2019

(65) Prior Publication Data
US 2020/0181782 A1 Jun. 11, 2020

Related U.S. Application Data

(60) Provisional application No. 62/538,256, filed on Jul. 28, 2017.

(51) Int. Cl.
C25B 3/05 (2021.01)
C25B 3/07 (2021.01)
(Continued)

(52) U.S. Cl.
CPC ............... *C25B 3/25* (2021.01); *C07C 51/15* (2013.01)

(58) Field of Classification Search
CPC .... C25B 3/30; C25B 3/05; C25B 3/07; C25B 3/25; C25B 3/26
(Continued)

(56) References Cited

U.S. PATENT DOCUMENTS 3,032,489 A 5/1962 Loveland
3,344,045 A * 9/1967 Neikam ................. C07C 51/00
205/442

(Continued)

FOREIGN PATENT DOCUMENTS

CN 104313631 A * 1/2015 ............... C25B 1/00
WO WO-2016/178590 A1 11/2016

OTHER PUBLICATIONS

Gambino et al., Electrochemical carboxylation of organic substrates—synthesis of carboxylic derivatives of acenaphthylene, J. Appl. Electrochem., 12(5):549-55 (1982).
(Continued)

*Primary Examiner* — Edna Wong
(74) *Attorney, Agent, or Firm* — MARSHALL, GERSTEIN & BORUN LLP

(57) ABSTRACT

The disclosure relates to methods for electrochemical reductive carboxylation of an unsaturated organic substrate to form a dicarboxylic organic product. The unsaturated organic substrate is electrochemically reduced with a carbon dioxide reactant in an ionically conductive, water-immiscible reactant medium to form the dicarboxylic organic product. The dicarboxylic organic product is recovered in an aqueous product medium. Example dicarboxylic organic products include phthalic acid, naphthalenedicarboxylic acid, furan-2,5-dicarboxylic acid, thiophene-2,5-dicarbox-
(Continued)

ylic acid, pyrrole-2,5-dicarboxylic acid, adipic acid, suberic acid, sebacic acid, and 1,12-dodecanedioic acid.

19 Claims, 9 Drawing Sheets

(51) Int. Cl.
  *C25B 3/25*    (2021.01)
  *C25B 3/26*    (2021.01)
  *C07C 51/15*   (2006.01)
(58) Field of Classification Search
  USPC .................. 205/440, 442, 422, 423, 427
  See application file for complete search history.

(56)  References Cited

U.S. PATENT DOCUMENTS

| | | | |
|---|---|---|---|
| 4,443,305 A * | 4/1984 | Haynes | C25C 1/00 205/352 |
| 4,455,208 A | 6/1984 | Holland | |
| 4,950,368 A | 8/1990 | Weinberg et al. | |
| 5,522,982 A | 6/1996 | Brietzke et al. | |
| 5,928,806 A * | 7/1999 | Olah | H01M 8/06 429/418 |
| 9,085,827 B2 | 7/2015 | Kaczur et al. | |
| 9,175,409 B2 | 11/2015 | Sivasankar et al. | |
| 2013/0118911 A1* | 5/2013 | Sivasankar | C25B 9/23 205/455 |
| 2014/0262792 A1* | 9/2014 | Rosenthal | C25D 5/54 205/50 |
| 2016/0017503 A1 | 1/2016 | Kaczur et al. | |

OTHER PUBLICATIONS

International Application No. PCT/US18/44014, International Search Report and Written Opinion, dated Oct. 10, 2018.
Banerjee A, et al., "Carbon dioxide utilization via carbonate-promoted C-H carboxylation", *Nature*, 531:215-33 (2016).
Kanan M. et al., "Carbonate-Catalyzed CO$_2$ Hydrogenation to Multi-Carbon Products", pp. 1-6 (2016).
Luca O.R. et al., "Organic reactions for the electrochemical and photochemical production of chemical fuels from CO$_2$—The reduction chemistry of carboxylic acids and derivatives as bent CO$_2$ surrogates", *J. Photochem. Photobiol., B*, pp. 1-17 (2015).
Matthessen R. et al., "Electrocarboxylation: towards sustainable and efficient synthesis of valuable carboxylic acids", *Beilstein J. Org. Chem.*, 10:2484-2500 (2014).
Scialdone O. et al., "An unexpected ring carboxylation in the electrocarboxylation of aromatic ketones", *Electrochim. Acta*, 51:3500-05 (2006).
Senboku H. et al., "Efficient Electrochemical Dicarboxylation of Phenyl-substituted Alkenes: Synthesis of 1-Phenylalkane-1,2-dicarboxylic Acids", *Synlett*, 3:418-20 (2001).
Sock O. et al., "Electosynthesis of Carboxylic Acids from Organic Halides and Carbon Dioxide", *Tetrahedron Letters*, 26(12):1509-12 (1985).
Wang H. et al., "Electrochemical carboxylation of cinnamate esters in MeCN", *Tetrahedron*, 64:314-18 (2008).
Li C-H et al., "Highyly regioselective electrochemical synthesis of dioic acids from dienes and carbon dioxide", *Electrochim. Acta*, 56(3):1529-34 (2011) (Abstract Only).
Ming H. et al., "Electrolytic reduction of phenanthrene", *Ranliao Huaxue Xuebao*, 22(2):219-23 (1994) (English Abstract Only).
Shul'zhenko G.I. et al., "Electrochemical synthesis of dicarboxylic acids via electroreduction of carbon dioxide in the presence of ethylene and its derivatives", *Izvestiya Akademii Nauk SSSR, Seriya Khimicheskaya*, 6:1377-80 (1991) (English Abstract Only).
Yuan G. et al., "Electrocarboxylation of carbon dioxide with polycyclic aromatic hydrocarbons using Ni as the cathode", *Chinese Journal of Chemistry*, 28.10, pp. 1983-1988 (2010) (English Abstract Only).
Elman A.R., "Synthesis Methods for 2,6-Naphthalenedicarboxylic Acid", *Catalysis in Industry*, 1(3):184-89 (2009).
Ticianelli E.A. et al., "The electrochemical characteristics of cathodic processes involving aromatic hydrocarbons and CO$_2$, Part I. General mechanistic considerations", *J. Electroanal. Chem.*, 258:369-77 (1989).
Ticianelli E.A. et al., "The electrochemical characteristics of cathodic processes involving aromatic hydrocarbons and CO$_2$, Part II. The ECE/DISP problem", *J. Electroanal. Chem.*, 258:379-89 (1989).
Gagyi Palffy E. et al., "Electrochemical reduction of polyaromatic compounds", *J. Appl. Electrochem.*, 24:337-43 (1994).
Kariv-Miller E. et al., "Electrochemical Hydrogenation and Hydrogenolysis in Aqueous Media, Final Report", DOE/PC/70807-T1; Order No. DE91 005742, pp. 1-16 (1989).
Kariv-Miller E. et al., "Electroreduction in Aqueous Media, Saturation of Polycyclic Aromatics", *Tetrahedron*, 42(8):2185-92 (1986).
Bré ant M. et al., "Study of the electrochemical reduction of aromatic polynuclear hydrocarbons in dimethylacetamide", *Anal. Chim. Acta*, 90:111-18 (1977) (English Abstract Only).
Lam C.H. et al., "Electrocatalytic upgrading of model lignin monomers with earth abundant metal electrodes", *Green Chem.*, 17:601-09 (2015).
Rabideau P.W. et al., "The Birch Reduction of Aromatic Compounds", *Org. React.*, 42:1-204 (1992).
Rosso J.A. et al., "Reactions of carbon dioxide radical anion with substituted benzenes", *J. Phys. Org. Chem.*, 14:300-09 (2001).

* cited by examiner

TPA

FDCA

NDCA

AA

PET

PEN

ELECTROCHEMICAL REDUCTIVE CARBOXYLATION OF UNSATURATED ORGANIC SUBSTRATES IN IONICALLY CONDUCTIVE MEDIUMS

CROSS REFERENCE TO RELATED APPLICATION

Benefit is claimed to U.S. Provisional Patent Application 62/538,256, filed Jul. 28, 2017, the entire disclosure of which is incorporated herein by reference.

BACKGROUND OF THE DISCLOSURE

Field of the Disclosure

The disclosure relates to methods for electrochemical reductive carboxylation of an unsaturated organic substrate to form a dicarboxylic organic product. The unsaturated organic substrate is electrochemically reduced with a carbon dioxide reactant in an ionically conductive, water-immiscible reactant medium to form the dicarboxylic organic product. The dicarboxylic organic product is recovered in an aqueous product medium.

Background

Terephthalic acid (TPA) is a starting material in syntheses of a range of materials, mostly polyethylene terephthalate (PET). In turn, PET is mostly used for the production of polyester fibers and carbonated beverage bottles, while other polyterephthalates provide dimensional stability, good heat resistance and durability for engineering applications. In addition, TPA is used as a raw material to make terephthalate plasticizers such as dioctyl terephthalate and dibutyl terephthalate. By 2006 global purified terephthalic acid demand was growing at rate of 6-8%/year. The relatively low current price of TPA can be ascribed to high production volumes, still-lasting availability of non-renewable resources (e.g., petroleum) for its feedstock, and the absence of a carbon dioxide tax. The plausible introduction of carbon dioxide tax, considered as a plausible measure to slow down the ongoing climate change, as well as reducing availability/increased cost of petroleum may increase the price of TPA, making it a less available or a less attractive commodity chemical.

SUMMARY

In an aspect, the disclosure relates to a method for electrochemical reductive carboxylation of an unsaturated organic substrate, the method comprising: (a) providing a reactant medium comprising a water-immiscible, ionically conductive, aprotic organic liquid (e.g., ionic liquid or otherwise), an unsaturated organic substrate reactant, and a carbon dioxide reactant (e.g., further including a supporting electrolyte); (b) providing a product medium comprising water (e.g., an aqueous product medium further including a supporting electrolyte); (c) electrochemically reducing the unsaturated organic substrate in the reactant medium with (i) a cathode in the reactant medium and (ii) an anode in the product medium, thereby forming a dicarboxylic organic product corresponding to the unsaturated organic substrate; and (d) recovering the dicarboxylic organic product in the product medium.

The reaction generally can be batch, semi-batch, or continuous. Providing the reactant medium can include feeding an organic liquid solution already containing the unsaturated organic substrate and carbon dioxide therein to a reaction vessel, feeding unsaturated organic substrate and/or carbon dioxide into an organic liquid medium already in the reaction vessel, continuously feeding organic liquid, unsaturated organic substrate, and carbon dioxide into the reaction vessel, etc. Electrochemical reduction can include applying a voltage differential or electrical current between the cathode and the anode, such as with power source in electrical connection with both electrodes. The dicarboxylic organic product can be in acid form (—COOH), anionic form (—COO), and/or salt form (—COOM, where M can be a metal such Na, K, or other alkali metal). The dicarboxylic organic product can be a single dicarboxylic species when the reduction or addition reaction is selective based on the unsaturated organic substrate reactant. The organic product can include multiple dicarboxylic species (e.g., positional isomers of each other) when the reduction or addition reaction is not selective or is only partially selective based on the unsaturated organic substrate reactant. The dicarboxylic organic product in the product medium can be recovered as a dissolved component in the water of the product medium (e.g., resulting from diffusion of the dicarboxylic organic product from the reactant medium where it is originally formed to the product medium where is it preferentially soluble in the polar aqueous product medium). The dicarboxylic organic product can be subsequently recovered/separated from the product medium by any suitable process, such as evaporation, concentration, crystallization, precipitation, etc.

The carbon dioxide reactant generally can include carbon dioxide itself ($CO_2$; dissolved or gaseous), a material capable of generating carbon dioxide in the reactant medium, or a material providing carboxylate groups in the reactant medium. Carbon dioxide may be introduced into the reactant medium as a gas (e.g., a dissolved gas; dispersed bubbles that dissolve in the reactant medium), or produced in situ in the reactant, for example via thermal decomposition of bicarbonate ions ($HCO_3$)) or electrochemical oxidation of formate ions ($HCOO^-$) or oxalate ions ($(COO)_2^{2-}$), any of which can be provided in the reactant medium in the form or their corresponding salts or acids. Other species such as carbonate esters (e.g., dimethyl carbonate, diethyl carbonate, ethylene carbonate, propylene carbonate) may be used instead of gaseous carbon dioxide. Formates and oxalates may be used to incorporate carboxylate groups into the substrate molecules via thermal reactions.

Various refinements of the methods for electrochemical reductive carboxylation are possible.

In a refinement, the organic liquid is selected from the group consisting of an ionic liquid, an organic solvent comprising a dissolved electrolyte, a liquid polymer comprising a dissolved electrolyte, a water-insoluble polymeric electrolyte (e.g., such as a pure liquid ionic polymer or mixtures of ionic polymer(s) with other poorly soluble organic compounds), and combinations thereof.

In a refinement, the organic liquid comprises an ionic liquid comprising (i) a cation selected from the group consisting of a substituted ammonium cation, a substituted phosphonium ion, a substituted sulfonium ion, a substituted aromatic heterocyclic ring having at least one quaternary ammonium cation, and combinations (e.g., mixtures) thereof, and (ii) a counter anion to the cation. Example ionic liquid components include: substituted ammonium cations (e.g., $NR_4^+$, where each R group independently can be H, a linear or branched alkyl group of 1 to 20 carbon atoms (e.g., substituted or unsubstituted; such as at least 1, 2, 3, 4, 6, 8, 10, or 12 carbon atoms and/or up to 2, 3, 4, 6, 8, 10, 12, 14, 16, 18, or 20 carbon atoms), or an aryl group of 6 to 20 carbon atoms (e.g., substituted or unsubstituted; such as at least 6, 10, or 14 carbon atoms and/or up to 8, 12, 16, 18, or 20 carbon atoms); preferably at least one R group is other than H (an alkyl or aryl group)); substituted phosphonium cations (e.g., $PR_4^+$, where each R group independently can be as described for the substituted ammonium cation, preferably with at least one R group other than H); substituted sulfonium cations (e.g., $SR_3^+$, where each R group independently can be as described for the substituted ammonium cation, preferably with at least one R group other than H); and substituted aromatic heterocyclic rings (e.g., pyridinium, pyridazinium, pyrimidinium, pyrazinium, oxazinium, thiazinium, imidazolium, pyrazolium, thiazolium, isothiazolium, oxazolium, isoxazolium, or triazolium groups substituted with one or more R groups as described for the substituted ammonium cation (e.g., substituted at a ring carbon atom and/or a ring heteroatom such as nitrogen), preferably with at least one R group other than H (e.g., substituted on the ring nitrogen heteroatom forming the quaternary ammonium group)). The counter ion can be selected from the group consisting of $F^-$, $Cl^-$, $Br^-$, $I^-$(e.g., halides more generally), $CN^-$, $NCS^-$, $NCO^-$, $OCN^-$, $(CF_3SO_2)_2N^-$, $BF_4^-$, $PF_6^-$, and combinations (e.g., mixtures) thereof. Ionic liquid is preferably insoluble or only sparingly soluble in water to limit loss/transport of ionic liquid to the aqueous phase during reaction.

In a refinement, the organic liquid comprises an organic solvent comprising a dissolved electrolyte. The organic solvent containing dissolved electrolyte can include (i) an organic solvent such as an ether, an ester, a dialkylcarbonate, a substituted amide, a ketone, a substituted sulfonamide, a substituted urea, and/or a substituted phosphoramide, and (ii) an electrolyte dissolved in the solvent. Examples of the organic solvents include tetrahydrofuran, 2-methyltetrahydrofuran, ethyl acetate, dimethylcarbonate, diethylcarbonate, ethylene carbonate, propylene carbonate (any of the isomers), N,N'-dimethylformamide, N,N'-dimethylacetamide, N-methylpyrrolidone, acetone, methylethylketone, methylisobutylketone, diisobutylketone, cyclohexanone, N,N,N'N'-tetramethylsulfamide, N,N,N'N'-tetraethylsulfamide, ethyltrimethylsulfamide, all isomers of diethyldimethylsulfamide, triethylmethylsulfamide, tetramethylurea, tetraethylurea, 1,3-dimethyl-2-imidazolidinone, tetrahydro-1,3-dimethyl-2(1H)-pyrimidinone, hexamethylphosphoramide, related compounds with different alkyl groups, and combinations (e.g., mixtures) thereof. Examples of the electrolytes include $Li^+$, $Na^+$, $K^+$, $Rb^+$, $Cs^+$ (e.g., alkali metals more generally), substituted ammonium cations as described above for ionic liquids, substituted phosphonium cations as described above for ionic liquids, substituted sulfonium cations as described above for ionic liquids, and substituted aromatic heterocyclic rings as described above for ionic liquids. The counter ion for the electrolyte can be selected from the group consisting of $F^-$, $Cl^-$, $Br^-$, $I^-$ (e.g., halides more generally), $CN^-$, $NCS^-$, $NCO^-$, $OCN^-$, $(CF_3SO_2)_2N^-$, $BF_4^-$, $PF_6^-$, and combinations (e.g., mixtures) thereof.

In a refinement, the organic liquid comprises a liquid polymer comprising a dissolved electrolyte. Examples of liquid polymers include polyethers and polyamides, such as polyethylene glycol, polypropylene glycol, their copolymers and oligomers, N-alkylated nylons (polyamides), and/or poly-N-vinylpyrrolidone. The same inorganic electrolyte as described above can be used to render the polymers electrically conductive. In this case, the aqueous solution preferably contains a sufficient concentration of electrolyte to suppress the solubility of the polymers in the aqueous phase.

In a refinement, the organic liquid comprises a water-insoluble polymeric electrolyte. Examples of water-insoluble polymeric electrolytes include polyalkylated quaternary polyamines, such as poly-N,N'-dialkyl-hexahydro-1H-azepine, poly-N,N'-dialkylethyleneimine, poly-N,N'-dialkylpropylenediamine, poly-N,N'-dialkylazacyclotridecane and other compounds. The quaternary nitrogen atoms in such polymers may be components of pyrrolidine, piperidine, morpholine, or other heterocyclic systems. The counter ion for the electrolyte can be selected from the group consisting of $F^-$, $Cl^-$, $Br^-$, $I^-$ (e.g., halides more generally), $CN^-$, $NCS^-$, $NCO^-$, $OCN^-$, $(CF_3SO_2)_2N^-$, $BF_1^-$, $PF_6^-$, and combinations (e.g., mixtures) thereof.

In a refinement, the unsaturated organic substrate reactant comprises at least one of an aromatic hydrocarbon substrate, a heteroaromatic hydrocarbon substrate (e.g., with one or more N, O, or S ring substituents), an alkylenic hydrocarbon substrate, and an alkylynic hydrocarbon substrate. The organic substrate can include mixture of different unsaturated reactant compounds and/or reactant compounds with more than one type of saturation. The hydrocarbon substrate in any form can have 2-30 carbon atoms, such at least 2, 3, 4, 6, 8, 10, or 12 carbon atoms and/or up to 4, 8, 12, 16, 20, 24, or 30 carbon atoms. The hydrocarbon substrate in any form can be substituted by 1, 2, or more than two groups including alkyl groups or oxygen-containing groups such as a carboxylic group (—COOH), an aldehyde group (—CHO), a hydroxyl group (—OH), and/or an alkoxy group (—OR such as methoxy, ethoxy, propoxy, or other higher alkoxy/ether group). Example unsaturated organic substrate reactants include: aromatic hydrocarbon (e.g., benzene, naphthalene, phenanthrene, p-terphenyl, chrysene, picene, anthracene, 9,10-diphenylanthracene, benzo(a)perylene, pyrene); substituted aromatic compounds (e.g., toluene, benzoic acid, benzaldehyde, phenol, 4-hydroxybenzoic acid); heteroaromatic hydrocarbons (e.g., furan, furfural, 2-furancarboxylic acid, thiophene, pyridine, 2-thiophenecarboxylic acid); alkylenic hydrocarbons (e.g., linear or branched hydrocarbon including 1, 2, or more than 2 C=C groups); and alkylynic hydrocarbons (e.g., linear or branched hydrocarbon including 1, 2, or more than 2 CC groups).

In a further refinement, the unsaturated organic substrate reactant comprises a substituted or unsubstituted benzene (e.g., benzene substituted with 0 or 1 carboxylic groups and optionally 1 or more alkyl groups or other oxygen-containing groups; such as benzoic acid, benzaldehyde, phenol, 4-hydroxybenzoic acid); and the dicarboxylic organic product comprises phthalic acid (e.g., including terephthalic acid (TPA) as a product component, preferably as substantially the only dicarboxylic organic product isomer present).

In a further refinement, the unsaturated organic substrate reactant comprises a substituted or unsubstituted naphthalene (e.g., naphthalene substituted with 0 or 1 carboxylic groups and optionally 1 or more alkyl groups or other oxygen-containing groups); and the dicarboxylic organic product comprises naphthalenedicarboxylic acid (e.g., including 2,6-naphthalenedicarboxylic acid (NDCA) as a product component, preferably as substantially the only dicarboxylic organic product isomer present, whether as originally formed in the reactant medium or after a subsequent thermal isomerization step of a corresponding potassium or other alkali salt of a mixture of naphthalenedicarboxylic acid isomers).

In a further refinement, the unsaturated organic substrate reactant comprises a substituted or unsubstituted furan (e.g., furan substituted with 0 or 1 carboxylic groups, aldehyde or hydroxymethyl group); and the dicarboxylic organic product comprises furandicarboxylic acid (e.g., including 2,5-furandicarboxylic acid (FDCA) as a product component, preferably as substantially the only dicarboxylic organic product isomer present).

In a further refinement, the unsaturated organic substrate reactant comprises a substituted or unsubstituted thiophene (e.g., thiophene substituted with 0 or 1 carboxylic groups, aldehyde or hydroxymethyl group); and the dicarboxylic organic product comprises a thiophenedicarboxylic acid (e.g., including 2,5-thiophenedicarboxylic acid as a product component, preferably as substantially the only dicarboxylic organic product isomer present).

In a further refinement, the unsaturated organic substrate reactant comprises a substituted or unsubstituted pyrrole (e.g., pyrrole substituted with 0 or 1 carboxylic groups, aldehyde or hydroxymethyl group); and the dicarboxylic organic product comprises a pyrroledicarboxylic acid (e.g., including 2,5-pyrroledicarboxylic acid as a product component, preferably as substantially the only dicarboxylic organic product isomer present).

In a further refinement, the unsaturated organic substrate reactant comprises one or more of ethylene, acetylene, and 1,3-butadiene; and the dicarboxylic organic product comprises at least one of adipic acid (1,6-hexanedioic acid, AA), suberic acid (1,8-octanedioic acid), sebacic acid (1,10-decanedioic acid), and 1,12-dodecanedioic acid. The dicarboxylic organic product can result from electrocatalytic reduction of an alkylenic hydrocarbon or an alkylynic hydrocarbon, optionally including subsequent step-wise oligomerization to form adipic or other acid with the desired carbon chain length, and optionally including subsequent hydrogenation to remove residual unsaturation.

In a refinement, electrochemically reducing the unsaturated organic substrate in the reactant medium in part (c) further comprises forming a formic reaction product (e.g., formic reaction product can be in acid form (HCOOH; formic acid), anionic form (HCOO⁻, formate), salt form (HCOOM; metal formate where M can be a metal such Na, K, other alkali metal, or an organic cation). In a further refinement, recovering the dicarboxylic organic product in part (d) further comprises recovering the formic reaction product in the product medium (e.g., analogous to the dicarboxylic organic product, the formic reaction product can be recovered as a dissolved component in the water of the product medium; resulting from diffusion of the formic reaction product from the reactant medium where it is originally formed to the product medium where is it preferentially soluble in the polar aqueous product medium). In a yet further refinement, the method further comprises: electrochemically oxidizing the formic reaction product in the product medium with the anode, thereby forming carbon dioxide as an oxidation product (e.g., electrochemical oxidation results from the same voltage differential or electrical current applied between the cathode and the anode for electrochemical reduction in the reactant medium); and recovering the carbon dioxide from the product medium in the reactant medium (e.g., $CO_2$ gas formed in the product medium such as at the anode can be transferred back to the reactant medium (e.g., dispersed bubbles buoyantly traveling from product medium to the reactant medium, such as when the product medium is the denser medium), thus providing a recycle/recovery means of $CO_2$ reactant that would otherwise be lost or discharged as formic acid waste).

In a refinement, the reactant medium and the product medium are in direct liquid-liquid contact. In another refinement, the cathodic electrolyte can be formed from a polymer, for example a thin polymeric membrane formed from water-insoluble, potentially cross-linked cationic polymer (e.g., as described above).

In a refinement, the reactant medium (e.g., the catholyte) is substantially free from water (e.g., less than 10, 5, 2, 1, or 0.1 wt. % of water in the reactant medium; alternatively or additionally less than 10, 5, 2, 1, or 0.1 wt. % in the reactant medium of materials other than the organic liquid, the unsaturated organic substrate reactant, the carbon dioxide reactant, any optional further supporting electrolyte in the reactant medium, and any dicarboxylic organic product present in the reactant medium after formation but prior to recovery in the product medium). In another refinement, the product medium (e.g., the anolyte) is substantially free from the organic liquid (e.g., organic solvents, polymers, and/or ionic liquids) constituting the catholyte (e.g., less than 10, 5, 2, 1, or 0.1 wt. % of organic liquids in the product medium).

In a refinement, the reactant medium further comprises a supporting electrolyte. In some cases, the reactant medium (catholyte) can be an ionic liquid or a cationic polymer, and it does not require an additional electrolyte. In some cases, the reactant medium can be an organic solvent or a non-ionic polymer, it which case it can further include a dissolved electrolyte as described above.

In a refinement, the product medium further comprises a supporting electrolyte (e.g., a saturated aqueous solution of an inorganic salt or other electrolyte; example includes potassium bicarbonate). For example, the aqueous phase of the product medium may contain additional electrolyte(s) that will suppress the solubility of the organic catholyte components and increase the conductivity of the aqueous phase. Also, the dissolved salts will participate in the chemical reactions resulting in formation of dicarboxylic acids and their derivatives. In addition, the dissolved electrolytes may reduce the oxygen evolution overvoltage. The cations in the aqueous electrolyte can include sodium and/or potassium cations. The anions can include formate, oxalate, carbonate, bicarbonate, phosphate, hydrophosphate, dihydrophosphate, borate, or sulfate ions.

In a refinement, the cathode comprises at least one of tin, bismuth, gallium, indium, copper, silver, gold, cadmium, mercury, and lead (e.g., more generally any metal or alloy characterized by a high hydrogen evolution overvoltage); and the anode comprises at least one of nickel, stainless steel, and ruthenium-doped titania (e.g., more generally any material capable to withstand the electrolysis conditions for an extended period of time, and also sufficiently reduce the oxygen evolution overvoltage. Any anode material used for water electrolysis can be used in the process described herein).

In various refinements, it can be desirable to perform the process at an elevated pressure to increase the concentration of the dissolved carbon dioxide, resulting in high rate of $CO_2^-$ generation and, overall, high equipment productivity. At the same time it can be desirable to perform the electrolysis at an elevated temperature to ensure sufficiently high rate of diffusion of the mixture components to each other, reduce the energy losses due to the Ohmic heating of the electrolytes, and also reduce the overpotentials due to of the water electrooxidation process.

In another aspect, the disclosure relates to a reaction system for electrochemical reductive carboxylation of an unsaturated organic substrate, the system comprising: (a) a reaction vessel having an interior volume and defining (i) a product region in the interior volume and (ii) a reactant region in the interior volume (e.g., reactant region being positioned above product region relative to a direction of gravity for normal operation of the reaction vessel); (b) a cathode positioned in the reactant region (e.g., and positioned/adapted to contact the reactant medium when present in the reaction vessel); (c) an anode positioned in the product region (e.g., and positioned/adapted to contact the product medium when present in the reaction vessel); (d) an electrical power source in electrical contact with the cathode and the anode (e.g., external to the reaction vessel; adapted to apply a voltage or electrical current between the cathode and the anode); (e) a source of reactant medium in fluid communication with the reactant region of the reaction vessel, the reactant medium comprising an ionic liquid, an unsaturated organic substrate reactant, and carbon dioxide reactant (e.g., source of reactant medium can be a single source/inlet of the reactant medium components as a mixture, or it can be multiple sources/inlets to feed the reactant medium components separately or in subcombination for mixing in the reactant region of the reaction vessel); and (f) a source of product medium in fluid communication with the product region of the reaction vessel, the product medium comprising water (e.g., source of product medium can be a single source/inlet of the product medium components as a mixture, or it can be multiple sources/inlets to feed the product medium components separately or in subcombination for mixing in the product region of the reaction vessel). The reaction system can be used to perform the disclosed methods for electrochemical reductive carboxylation of an unsaturated organic substrate in any of their variously disclosed embodiments and refinements.

While the disclosed compounds, methods, compositions, apparatus, and systems are susceptible of embodiments in various forms, specific embodiments of the disclosure are illustrated (and will hereafter be described) with the understanding that the disclosure is intended to be illustrative, and is not intended to limit the claims to the specific embodiments described and illustrated herein.

BRIEF DESCRIPTION OF THE DRAWINGS

FIG. 4 panels b and c illustrate intermediate products of the mechanism.

DETAILED DESCRIPTION

The disclosure generally relates to methods for electrochemical reductive carboxylation of an unsaturated organic substrate. The method can include providing a reactant medium including a water-immiscible, ionically conductive aprotic organic liquid, an unsaturated organic substrate reactant, and a carbon dioxide reactant, providing a product medium including water, electrochemically reducing the unsaturated organic substrate in the reactant medium with (i) a cathode in the reactant medium and (ii) an anode in the product medium, thereby forming a dicarboxylic organic product corresponding to the unsaturated organic substrate, and recovering the dicarboxylic organic product in the product medium.

Figure 1:
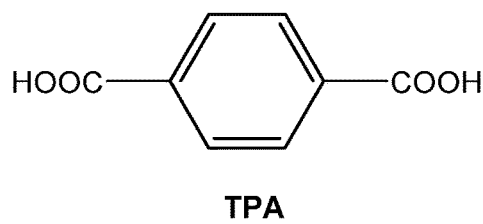
FIG. 1 shows the structures of exemplary dicarboxylic acids, such as, terephthalic acid (TPA), 2,6-naphthalenedicarboxylic acid (NDCA), furan-2,5-dicarboxylic acid (FDCA), and adipic acid (AA).
Figure 1:
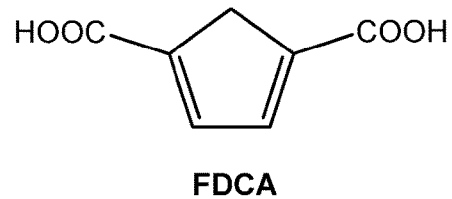
Figure 1:
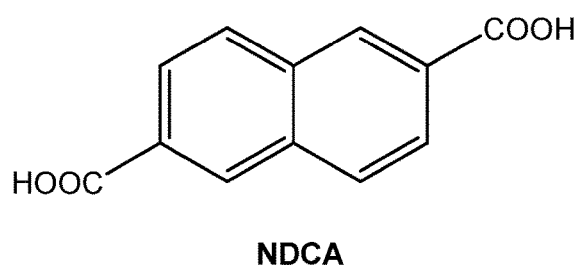
Figure 1:
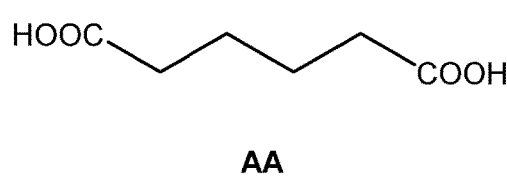

The methods of the disclosure can be useful in the synthesis of dicarboxylic acids, such as, but not limited to, terephthalic acid (TPA), furan-2,5-dicarboxylic acid (FDCA), 2,6-naphthalenedicarboxylic acid (NDCA), and adipic acid (AA). The structures of these acids are illustrated in FIG. 1.

The development of carbon-neutral TPA, AA, FDCA and NDCA production processes from renewable resources, such as plant biomass, would help ensure the continuity of the production of these products, even in the likely and eventual event of a carbon dioxide tax, or in a post-oil era. Consequently, using the methods disclosed herein, the current and future availability of PET and PEN production can be ensured.

Figure 2:
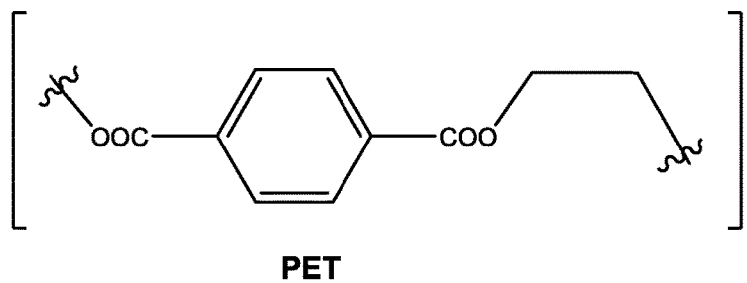
FIG. 2 shows the structures of polyethylene terephthalate (PET) and polyethylenenaphthalate (PEN).
Figure 2:
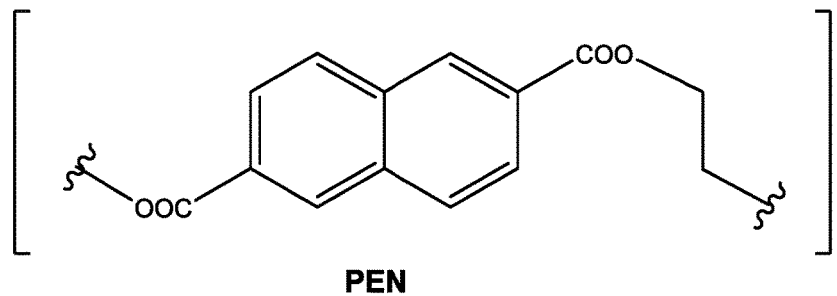

Polyethylenenaphthalate (PEN), as shown in FIG. 2, is made from NDCA, and is related to PET, but exhibits higher strength, higher thermal stability, and five times lower carbon dioxide permeability than PET. In addition to replacing PET in the food industry, the superior thermal, mechanical, and vapor barrier properties of NDCA-containing polyesters, like PEN, make them useful in the high-performance films of solar panels. Additionally, the utilization of light, strong, and stable materials based on NDCA in the car industry can reduce the weight of the cars, reduce fuel consumption, and increase the car's longevity.

The abundance of heavy oils in Canada and Venezuela, and the presence of naphthalene in products of its pyrolysis, catalytic biomass pyrolysis, and in coal tars help guarantee its long-term supply from renewable sources. However, as with TPA, there currently exists no selective, straightforward, high-yield methods for the synthesis of NDCA from naphthalene. Instead, most of the 2,6-NDCA synthesis processes currently developed are based on the catalytic oxidation of alkylnaphthalenes and suffer from a number of drawbacks, such as the necessity of performing the process in several steps and low selectivity.

Additional renewable and important starting materials used in the synthesis of polymeric materials include FDCA and AA. FDCA can be an important renewable building block because it can substitute for TPA in the production of polyesters and other current polymers containing an aromatic moiety. However, like in the case with TPA and NDCA described above, the high cost and lack of economical synthesis procedure prevent its large-scale production and application.

Adipic acid is used in nylon synthesis, as well as in the syntheses of other polymers. From an industrial perspective, adipic acid is the most important dicarboxylic acid, as about 2.5 billion kilograms of it are produced annually.

Adipic acid, terephthalic acid, furan-2,5-dicarboxylic acid, and 2,6-naphthalenediocarboxylic acid all share a common feature: their molecules have central cores to which couples of carboxylate groups are attached from the opposite side. The development of a general procedure for the synthesis of such dicarboxylic acids can allow the establishment of a series of industrial processes for the synthesis of these substances. The utilization of renewable feedstock, gaseous carbon dioxide, and renewable electricity for those syntheses can help ensure the security of the production from the oil supplies, as well as oil price fluctuations. When a carbon dioxide tax is introduced, if ever, the methods according to the disclosure can help ensure an economical advantage from the tax, in comparison with the presently used production methods of TPA, AA, FDCA, NDCA, and the like.

The synthesis of dicarboxylic acids as described herein includes the generation of either carboanions or $CO_2^-$ radical anions, for example from a carbon dioxide reactant (e.g., carbon dioxide or a source thereof). Both of these species can coexist for the time sufficient to form carboxylic acids in a reactant medium when in aprotic media. In the disclosed method, an aqueous product medium is present to ensure the high electrical conductivity of the system and the release of innocuous $O_2$ on the anode. Thus, the reactant medium has low solubility or miscibility with water. The low solubility can be achieved by providing a reactant medium as described in more detail below.

Reactant Medium

In embodiments, the reactions according to the disclosed method are performed in a reactant medium including a water-immiscible, ionically conductive, aprotic organic liquid, an unsaturated organic substrate reactant, and a carbon dioxide reactant.

Organic Liquid

Reductive electrochemical carboxylation is unlikely to take place in aqueous solutions due to the generally negligible solubility of the organic substrate reactants, such as benzene and naphthalene, in water. However, electroreductive hydrogenation of, for example, phenanthracene can be performed in polar solvents, including aqueous solutions. Without intending to be bound by theory, by including polar organic solvents or tetraalkylammonium cations in these solutions, the solubility of the neutral phenanthracene molecules can be increased, while simultaneously decreasing the rates of the water reduction on the cathode. Therefore, by the addition of an organic component, that is an organic liquid, to the reactant medium of the methods according to the disclosure, the solubility of poorly soluble organic substrate reactants can be increased, and the rate of protonation of the carboanions and $CO_2^-$ radical-anion can be decreased, enabling it to react with the organic substrate reactants, leading to the precursors of the dicarboxylic acids.

The water-immiscible, ionically conductive, aprotic organic liquid is not particularly limited. Examples of the organic liquid include, but are not limited to, ionic liquids, organic solvents including dissolved electrolytes, liquid polymers including dissolved electrolytes, water-insoluble polymeric electrolytes, or combinations thereof.

Water-insoluble polymeric electrolytes can include, for example, pure liquid ionic polymers or mixtures of ionic polymers with other poorly soluble organic compounds.

In embodiments wherein the organic liquid is an ionic liquid, the ionic liquid can include a cation. Examples of suitable cations include, but are not limited to, substituted ammonium cations, substituted phosphonium cations, substituted sulfonium cations, substituted aromatic heterocyclic rings having at least one quaternary ammonium cation, and combinations thereof.

Substituted ammonium cations include, for example $NR_4^+$, wherein each R group can independently be H, a linear or branched alkyl group of 1 to 20 carbons, or an aryl group of 6 to 20 carbons. When the R group is a linear or branched alkyl group, the alkyl group can include any number of carbon atoms between 1 and 20, for example from 1 to 20 carbons, from 2 to 18 carbons, from 3 to 16 carbons, from 4 to 14 carbons, from 5 to 13 carbons, from 6 to 12 carbons, from 7 to 11 carbons, or from 8 to 10 carbons, for example 1, 2, 3, 4, 5, 6, 7, 8, 9, 10, 11, 12, 13, 14, 15, 16, 17, 18, 19, or 20 carbons. Any one or more carbons of the linear or branched alkyl group can be substituted or unsubstituted. When the R group is an aryl group, the aryl group can include any number of carbon atoms between 6 and 20, for example from 6 to 20 carbons, from 7 to 18 carbons, from 8 to 16 carbons, from 9 to 14 carbons, from 10 to 13 carbons, or from 11 to 12 carbons, for example 6, 7, 8, 9, 10, 11, 12, 13, 14, 15, 16, 17, 18, 19, or 20 carbons. Any one or more carbons of the aryl group can be substituted or unsubstituted. In embodiments, at least one R group of the substituted ammonium cation is other than H, for example an alkyl or aryl group, as described above.

Substituted phosphonium cations include, for example $PR_4^+$, wherein each R group can independently be H, a linear or branched alkyl group of 1 to 20 carbons, or an aryl group of 6 to 20 carbons. When the R group is a linear or branched alkyl group, the alkyl group can include any number of carbon atoms between 1 and 20, for example from 1 to 20 carbons, from 2 to 18 carbons, from 3 to 16 carbons, from 4 to 14 carbons, from 5 to 13 carbons, from 6 to 12 carbons, from 7 to 11 carbons, or from 8 to 10 carbons, for example 1, 2, 3, 4, 5, 6, 7, 8, 9, 10, 11, 12, 13, 14, 15, 16, 17, 18, 19, or 20 carbons. Any one or more carbons of the linear or branched alkyl group can be substituted or unsubstituted. When the R group is an aryl group, the aryl group can include any number of carbon atoms between 6 and 20, for example from 6 to 20 carbons, from 7 to 18 carbons, from 8 to 16 carbons, from 9 to 14 carbons, from 10 to 13 carbons, or from 11 to 12 carbons, for example 6, 7, 8, 9, 10, 11, 12, 13, 14, 15, 16, 17, 18, 19, or 20 carbons. Any one or more carbons of the aryl group can be substituted or unsubstituted. In embodiments, at least one R group of the substituted phosphonium cation is other than H, for example an alkyl or aryl group, as described above.

Substituted sulfonium cations include, for example $SR_3^+$, wherein each R group can independently be H, a linear or branched alkyl group of 1 to 20 carbons, or an aryl group of 6 to 20 carbons. When the R group is a linear or branched alkyl group, the alkyl group can include any number of carbon atoms between 1 and 20, for example from 1 to 20 carbons, from 2 to 18 carbons, from 3 to 16 carbons, from 4 to 14 carbons, from 5 to 13 carbons, from 6 to 12 carbons, from 7 to 11 carbons, or from 8 to 10 carbons, for example 1, 2, 3, 4, 5, 6, 7, 8, 9, 10, 11, 12, 13, 14, 15, 16, 17, 18, 19, or 20 carbons. Any one or more carbons of the linear or branched alkyl group can be substituted or unsubstituted. When the R group is an aryl group, the aryl group can include any number of carbon atoms between 6 and 20, for example from 6 to 20 carbons, from 7 to 18 carbons, from 8 to 16 carbons, from 9 to 14 carbons, from 10 to 13 carbons, or from 11 to 12 carbons, for example 6, 7, 8, 9, 10, 11, 12, 13, 14, 15, 16, 17, 18, 19, or 20 carbons. Any one or more carbons of the aryl group can be substituted or unsubstituted. In embodiments, at least one R group of the substituted sulfonium cation is other than H, for example an alkyl or aryl group, as described above.

Substituted aromatic heterocyclic rings include, for example, pyridinium, pyridazinium, pyrimidinium, pyrazinium, oxazinium, thiazinium, imidazolium, pyrazolium, thiazolium, isothiazolium, oxazolium, isoxazolium, or triazolium groups substituted with one or more R groups. Each R group can independently be H, a linear or branched alkyl group of 1 to 20 carbons, or an aryl group of 6 to 20 carbons. When the R group is a linear or branched alkyl group, the alkyl group can include any number of carbon atoms between 1 and 20, for example from 1 to 20 carbons, from 2 to 18 carbons, from 3 to 16 carbons, from 4 to 14 carbons, from 5 to 13 carbons, from 6 to 12 carbons, from 7 to 11 carbons, or from 8 to 10 carbons, for example 1, 2, 3, 4, 5, 6, 7, 8, 9, 10, 11, 12, 13, 14, 15, 16, 17, 18, 19, or 20 carbons. Any one or more carbons of the linear or branched alkyl group can be substituted or unsubstituted. When the R group is an aryl group, the aryl group can include any number of carbon atoms between 6 and 20, for example from 6 to 20 carbons, from 7 to 18 carbons, from 8 to 16 carbons, from 9 to 14 carbons, from 10 to 13 carbons, or from 11 to 12 carbons, for example 6, 7, 8, 9, 10, 11, 12, 13, 14, 15, 16, 17, 18, 19, or 20 carbons. Any one or more carbons of the aryl group can be substituted or unsubstituted. In embodiments, the ring can be substituted at a ring carbon atom and/or a ring heteroatom such as nitrogen. In embodiments, at least one R group of the aromatic heterocyclic ring is other than H. For example, the ring can be substituted on the ring nitrogen heteroatom forming the quaternary ammonium group as described above.

Advantageously, the alkyl chains present in the structure of the cations of the ionic liquid can balance the charge of the carboanions and/or $CO_2^-$ radical anions. An example of a commercial ionic liquid suitable for the methods of the disclosure is ALIQUAT 336, which is a methyl-, trialkyl-ammonium chloride ionic liquid, where the three alkyl groups other than methyl are generally a mixture octyl and decyl groups.

Furthermore, in embodiments wherein the organic liquid is an ionic liquid, the ionic liquid can further include a counter anion to the cation. Suitable counter ions include, but are not limited to, halides, such as $F^-$, $Cl^-$, $Br^-$, and $I^-$, as well as ions such as $CN^-$, $NCS^-$, $NCO^-$, $OCN^-$, $(CF_3SO_2)_2N^-$, $PF_6^-$, and combinations or mixtures thereof. In embodiments, the ionic liquid is insoluble or only sparingly soluble in water. Advantageously, an insoluble or only sparingly soluble ionic liquid can limit the loss and/or transport of the ionic liquid to the aqueous phase during the reaction.

Without intending to be bound by theory, the low polarity of the ionic liquids is expected to poorly solvate small inorganic anions, such as hydroxyl and bicarbonate groups. As a result, the potentials for the proton reduction in those liquids corresponding to Equations 1 and 2, below, will be negatively shifted. If the potentials are shifted to be more negative than that of carbon dioxide reduction into the $CO_2^-$ anion-radical, as shown in Equation 3, below, the radicals can then react with the organic substrate reactant to yield carboxylic acids.

$$2H_2O_3 + 2e^- \rightarrow H_2\uparrow + 2OH^- \tag{Equation 1}$$

$$2H_2CO_3 + 2e^- \rightarrow H_2\uparrow + 2HCO_3^- \tag{Equation 2}$$

$$CO_2 + e^- \rightarrow CO_2^- \tag{Equation 3}$$

In embodiments, the organic liquid includes an organic solvent including a dissolved electrolyte. Suitable examples of an organic solvent include, but are not limited to, an ether, an ester, a dialkylcarbonate, a substituted amide, a ketone, a substituted sulfonamide, a substituted urea, and a substituted phosphoramide. That is, the organic solvent can include, for example, tetrahydrofuran, 2-methyltetrahydrofuran, ethyl acetate, dimethylcarbonate, diethylcarbonate, ethylene carbonate, propylene carbonate (any of the isomers), N,N'-dimethyldormamide, N,N'-dimethylacetamide, N-methylpyrrolidone, acetone, methylethylketone, methylisobutylketone, diisobutylketone, cyclohexanone, N,N,N'N'-tetramethylsulfamide, N,N,N'N'-tetraethylsulfamide, ethyltrimethylsulfamide, all isomers of diethyldimethylsulfamide, triethylmethylsulfamide, tetramethylurea, tetraethylurea, 1,3-dimethyl-2-imidazolidinone, tetrahydro-1,3-dimethyl-2(1H)-pyrimidinone, hexamethylphosphoramide, related compounds with different alkyl groups, and combinations or mixtures of the foregoing. Examples of the electrolytes include alkali metals, such as $Li^+$, $Na^+$, $K^+$, $Rb^+$, and $Cs^+$, or other electrolytes such as substituted ammonium cations as described above for ionic liquids, substituted phosphonium cations as described above for ionic liquids, substituted sulfonium cations as described above for ionic liquids, and substituted aromatic heterocyclic rings as described above for ionic liquids. Suitable counter ions to the electrolyte can include, but are not limited to, halides, such as $F^-$, $Cl^-$, $Br^-$, and $I^-$, as well as ions such as $CN^-$, $NCS^-$, $NCO^-$, $OCN^-$, $(CF_3SO_2)_2N^-$, $PF_6^-$, and combinations or mixtures thereof.

In embodiments, the organic liquid includes a liquid polymer including a dissolved electrolyte. Suitable liquid polymers include, but are not limited to, polyethers and polyamides, such as, for example, polyethylene glycol (PEG), polypropylene glycol (PPG), their copolymers and oligomers, N-alkylated nylons, that is, polyamides, and poly-N-vinylpyrrolidone. Any suitable inorganic electrolyte that can render the liquid polymer electrically conductive can be considered suitable. For example, suitable electrolytes include alkali metals, such as $Li^+$, $Na^+$, $K^+$, $Rb^+$, and $Cs^+$, or other electrolytes such as substituted ammonium cations as described above for ionic liquids, substituted phosphonium cations as described above for ionic liquids, substituted sulfonium cations as described above for ionic liquids, and substituted aromatic heterocyclic rings as described above for ionic liquids. Suitable counter ions to the electrolyte can include, but are not limited to, halides, such as $F^-$, $Cl^-$, $Br^-$, and $I^-$, as well as ions such as $CN^-$, $NCS^-$, $NCO^-$, $OCN^-$, $(CF_3SO_2)_2N^-$, $BF_4^-$, $PF_6^-$, and combinations or mixtures thereof. Advantageously, when the aqueous solution contains a sufficient amount or concentration of the electrolyte, the solubility of the liquid polymers in the aqueous solution is suppressed.

In embodiments, the organic liquid includes a water-insoluble polymer electrolyte. Suitable examples of water-insoluble polymeric electrolytes include, but are not limited to polyalkylated quaternary polyamines, such as poly-N,N'-dialkyl-hexahydro-1H-azepine, poly-N,N'-dialkylethyleneimine, poly-N,N'-dialkylpropylenediamine, poly-N,N'-dialkylazacyclotridecane and other compounds. The quaternary nitrogen atoms in such polymers can be components of pyrrolidine, piperidine, morpholine, or other heterocyclic systems. Suitable counter ions to the electrolyte can include, but are not limited to, halides, such as $F^-$, $Cl^-$, $Br^-$, and $I^-$, as well as ions such as $CN^-$, $NCS^-$, $NCO^-$, $OCN^-$, $(CF_3SO_2)_2N^-$, $BF_4^-$, $PF_6^-$, and combinations or mixtures thereof.

Unsaturated Organic Substrate

The reaction medium in the methods according to the disclosure further includes an unsaturated organic substrate. The unsaturated organic substrate can include, for example, an aromatic hydrocarbon substrate, a heteroaromatic hydrocarbon substrate, an alkylenic hydrocarbon substrate, or an alkylynic hydrocarbon substrate. The heteroaromatic hydrocarbon substrate can include, for example, one or more N, S, or O atoms in the aromatic ring(s) of the hydrocarbon substrate.

The organic substrate can include mixtures of different unsaturated reactant compounds and/or mixtures of reactant compounds with more than one type of saturation. The hydrocarbon substrate can include from 2 to 30 carbon atoms, from 3 to 24 carbon atoms, from 4 to 20 carbon atoms, from 5 to 17 carbon atoms, from 7 to 15 carbon atoms, from 8 to 13 carbon atoms or from 9 to 11 carbon atoms, for example 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms.

The hydrocarbon substrate can be substituted by one, two, or more than two groups. For example, the hydrocarbon substrate can be substituted with alkyl groups or oxygen-containing groups, such as carboxylic acids, aldehydes, hydroxyls, and/or alkoxy groups, such as methoxy, ethoxy, propoxy, or other higher alkoxy or ether groups. In embodiments, the alkyl group (or alkyl portion of an alkoxy group) can be a linear or branched alkyl group, including any number of carbon atoms between 1 and 20, for example from 1 to 20 carbons, from 2 to 18 carbons, from 3 to 16 carbons, from 4 to 14 carbons, from 5 to 13 carbons, from 6 to 12 carbons, from 7 to 11 carbons, or from 8 to 10 carbons, for example 1, 2, 3, 4, 5, 6, 7, 8, 9, 10, 11, 12, 13, 14, 15, 16, 17, 18, 19, or 20 carbons.

Example of suitable aromatic hydrocarbon substrates include, but are not limited to, benzene, naphthalene, phenanthrene, p-terphenyl, chrysene, picene, anthracene, 9,10-diphenylanthracene, benzo(a)perylene and pyrene.

Examples of suitable heteroaromatic hydrocarbons include, but are not limited to, furan, furfural, 2-furancarboxylic acid, thiophene, pyridine, and 2-thiphenecarboxylic acid.

Examples of suitable alkylenic hydrocarbons include, but are not limited to linear or branched hydrocarbons including one, two, or more than two C=C alkene groups. Similarly, suitable examples of alkylynic hydrocarbons include, but are not limited to linear or branched hydrocarbons including one, two, or more than two C=C alkyne groups.

Carbon Dioxide Reactant

In the methods according to the disclosure, the reaction medium further includes a carbon dioxide reactant. The carbon dioxide reactant can generally include carbon dioxide itself, such as dissolved or gaseous carbon dioxide, a material capable of generating carbon dioxide in the reactant medium, or a material providing carboxylate groups in the reactant medium. Carbon dioxide may be introduced into the reactant medium as a gas, for example, as a dissolved gas or a gas dispersed as bubbles that dissolve in the reactant medium, or it can be produced in situ in the reactant. When produced in situ, the carbon dioxide reactant can be produced, for example, through thermal decomposition of bicarbonate ions ($HCO_3^-$) or electrochemical oxidation of formate ions ($HCOO^-$) or oxalate ions ($(COO)_2^{2-}$), any of which can be provided in the reactant medium in the form or their corresponding salts or acids. Other species such as carbonate esters may be used instead of gaseous carbon dioxide. Suitable examples of carbonates include, but are not limited to, dimethyl carbonate, diethyl carbonate, ethylene carbonate, and propylene carbonate. Furthermore, formates and oxalates may be used to incorporate carboxylate groups into the substrate molecules via thermal reactions.

Supporting Electrolyte

In embodiments, the reactant medium, or the "catholyte," can further include a supporting electrolyte. In some embodiments, the reactant medium can include an ionic liquid or a cationic polymer, and it does not require an additional electrolyte. In some embodiments, the reactant medium can include an organic solvent or a non-ionic polymer, and can further include a dissolved electrolyte, as described above.

In embodiments, the cathodic (i.e. reactant) electrolyte can be formed from a polymer, for example a thin polymeric membrane formed from water-insoluble, potentially cross-linked cationic polymer, as described above.

Furthermore, in embodiments, the reactant medium or catholyte, is substantially free from water. As used herein, "substantially free from water" can mean that the reactant medium contains less than about 10, less than about 5, less than about 2, less than about 1, or less than about 0.1 wt % water. Alternatively, or additionally, the term "substantially free from water" can mean that any component of the reactant medium other than the organic liquid, the unsaturated organic substrate reactant, the carbon dioxide reactant, any optional further supporting electrolyte, and any dicarboxylic organic product present in the reactant medium after formation but prior to recovery in the product medium contains less than about 10, less than about 5, less than about 2, less than about 1, or less than about 0.1 wt % water.

Product Medium

In methods according to the disclosure, the product medium is an aqueous medium. That is, the reaction medium includes water, in addition to the dicarboxylic organic product or products. Advantageously, the solubility differences between the reactant and product media allows for the separation and isolation of the dicarboxylic organic product, which is preferentially soluble in the product medium as compared to the reaction medium, at the completion of the electrochemical carboxylation method.

Dicarboxylic Organic Product

In embodiments according to the disclosure, the dicarboxylic organic product can be in acid form (—COOH), anionic form (—COO$^-$), and/or salt form (—COOM, wherein M can be a metal such Na, K, or other alkali metal). In embodiments, the dicarboxylic organic product can be a single dicarboxylic species when the reduction or addition reaction is selective based on the unsaturated organic substrate reactant. In embodiments, the organic product can include multiple dicarboxylic species (e.g., positional isomers of each other) when the reduction or addition reaction is not selective or is only partially selective based on the unsaturated organic substrate reactant.

In embodiments, the unsaturated organic substrate reactant includes a substituted or unsubstituted benzene. The benzene substrate can be substituted with up to one carboxylic group and optionally, one or more alkyl groups or other oxygen-containing groups (e.g., hydroxy, alkoxy, aldehyde group). Suitable examples of the benzene substrate include, but are not limited to benzoic acid, benzaldehyde, phenol, and 4-hydroxybenzoic acid. Exemplary starting materials of benzene-containing organic substrate reactants are shown in panels a-g of FIG. 8.

Figure 3:
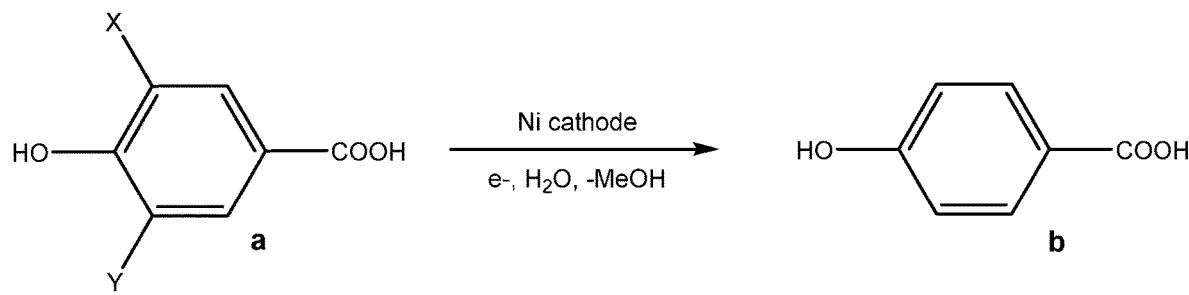
FIG. 3 illustrates the electrocatalytic demethoxylation of lignin-derived acids (panel a) into para-hydroxybenzoic acid (PHBA) (panel b).
Figure 4:
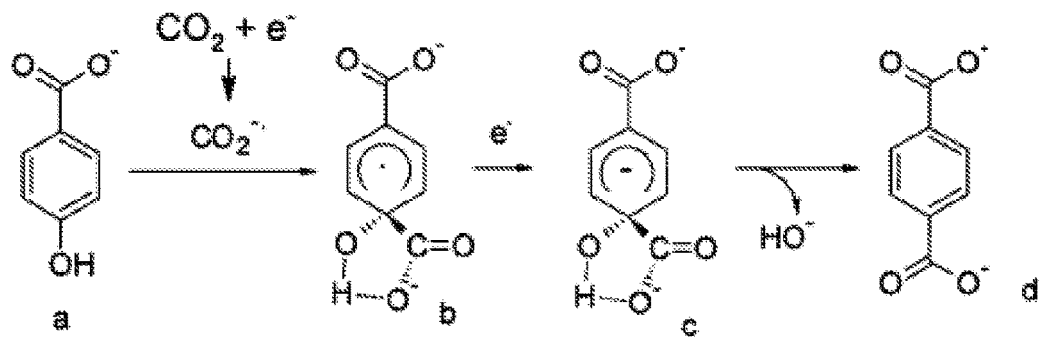
FIG. 4 illustrates a mechanism of PHBA (panel a) reductive carboxylation in ionic liquid (IL) into TPA dianions (panel d).
Figure 5:
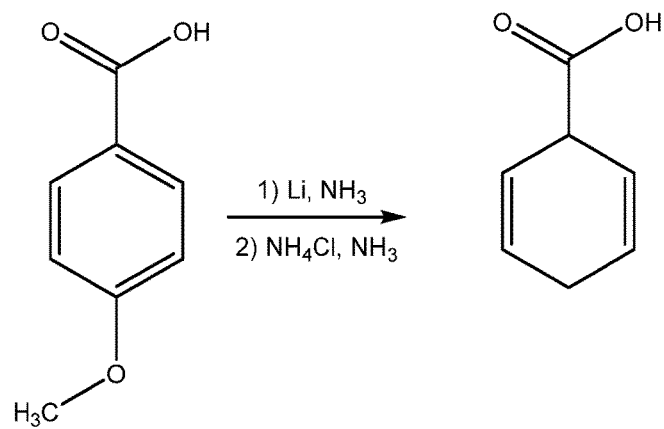
FIG. 5 illustrates the loss of the leaving group via Birch reduction.

In embodiments, the unsaturated organic substrate reactant can include lignin oxidation products. For example, the oxidation of lignin, the second most abundant biorenewable polymer, generates a mixture of monocarboxylic acids (See FIG. 3, wherein X, Y=H, OMe). Without intending to be bound by theory, it is expected that the electrocatalytic demethoxylation of those compounds yields parahydroxybenzoic acid (PHBA), as shown in FIG. 3. Subsequent electroreductive carboxylation of PHBA according to the methods of the disclosure can yield terephthalic acid, as shown by the mechanism in FIG. 4. As illustrated in FIG. 4, when extracted into the reactant medium, PHBA is predominantly present in the form of monoanions. The deprotonation of the phenolic groups can be suppressed by the low solvation energy of the dianions in the reactant medium. The carbon dioxide radical anions can attach to the PHBA anions, thereby increasing the distance between the negative charges, that is, in the para-position relative to the ionized carboxylate group, as shown in FIG. 4. The resulting anions can be stabilized by intramolecular hydrogen bonding to the hydroxide group, and subsequent reductive dehydroxylation can result in the formation of terephthalate anions, as shown in FIG. 4 (panel d). The loss of the electron withdrawing group in the para-position to the carboxylate group, as shown in FIG. 5, can take place during Birch reduction.

In embodiments wherein the unsaturated organic substrate reactant includes a benzene substrate as described above, the dicarboxylic organic product can include phthalic acid. That is, the dicarboxylic organic product can include, for example, terephthalic acid (TPA) as a product component. Preferably, in these embodiments, the dicarboxylic organic product includes terephthalic acid as substantially the only dicarboxylic organic product isomer.

Because polyanions, such as TPA, have much higher hydration enthalpy than monoanions, such as PHBA, the TPA anions originally formed in the reactant medium can preferentially diffuse into the aqueous product medium as compared to the PHBA anions, facilitating the separation of the TPA from the reactant medium and corresponding recovery in the product medium.

Figure 6:
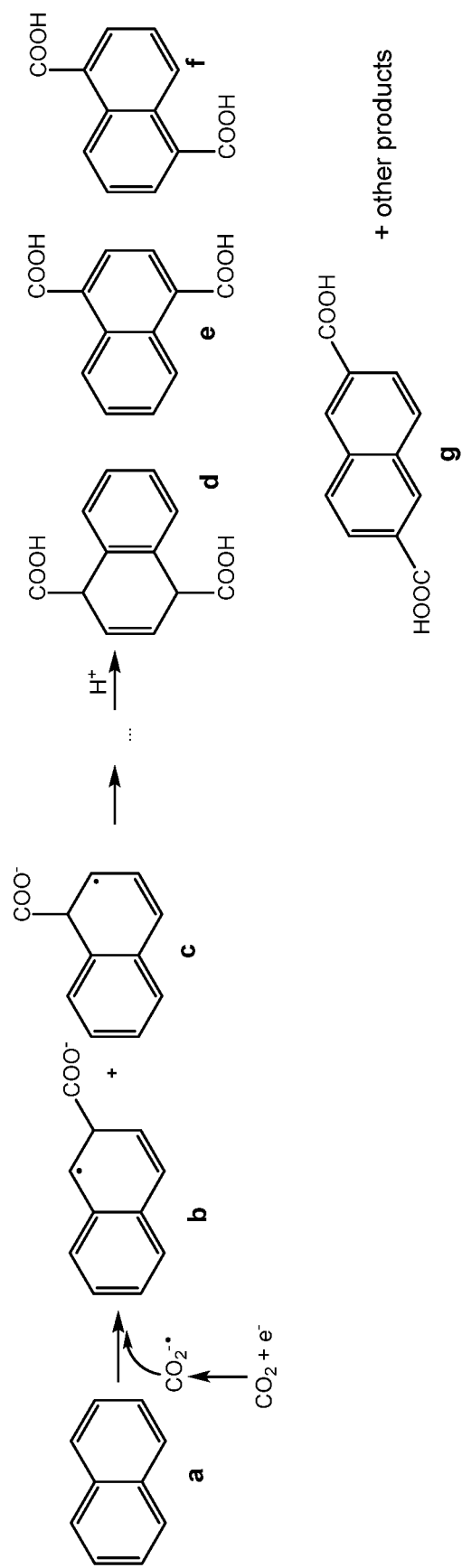
FIG. 6 illustrates the synthesis of naphthalenedicarboxylic acids (panels d-g) via electroreduction of naphthalene-$CO_2$ system (panels a-c).
Figure 7:
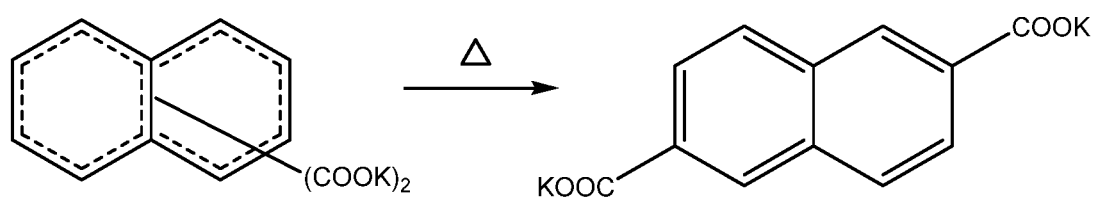
FIG. 7 shows the isomerization of potassium salts of naphthalenedicarboxylic acids.

In embodiments, the unsaturated organic substrate reactant includes a substituted or unsubstituted naphthalene. The naphthalene substrate can be substituted with up to one carboxylic group and optionally, one or more alkyl groups or other oxygen-containing groups (e.g., hydroxy, alkoxy, aldehyde group). In embodiments wherein the unsaturated organic substrate reactant includes a naphthalene substrate as described above, the dicarboxylic organic product can include naphthalenedicarboxylic acid. That is, the dicarboxylic organic product can include, for example, 2,6-naphthalenedicarboxylic acid (NDCA) as a product component. Preferably, in these embodiments, the dicarboxylic organic product includes 2,6-naphthalenecarboxylic acid as substantially the only dicarboxylic organic product isomer, as shown in panel g of FIG. 6. The NDCA can be present as a naturally formed product of the reaction, or it can be formed after a subsequent isothermal isomerization step of a corresponding potassium or other alkali metal salt of a mixture of various naphthalenedicarboxylic acid isomers, as shown in FIG. 7.

In embodiments, the unsaturated organic substrate reactant includes a substituted or unsubstituted furan. The furan substrate can be substituted with up to one of each of carboxylic group, aldehyde group, and/or hydroxymethyl group. Suitable starting materials for the reductive carboxylation of a furan-containing organic substrate reactant are shown in panels h-j of FIG. 8.

Figure 8:
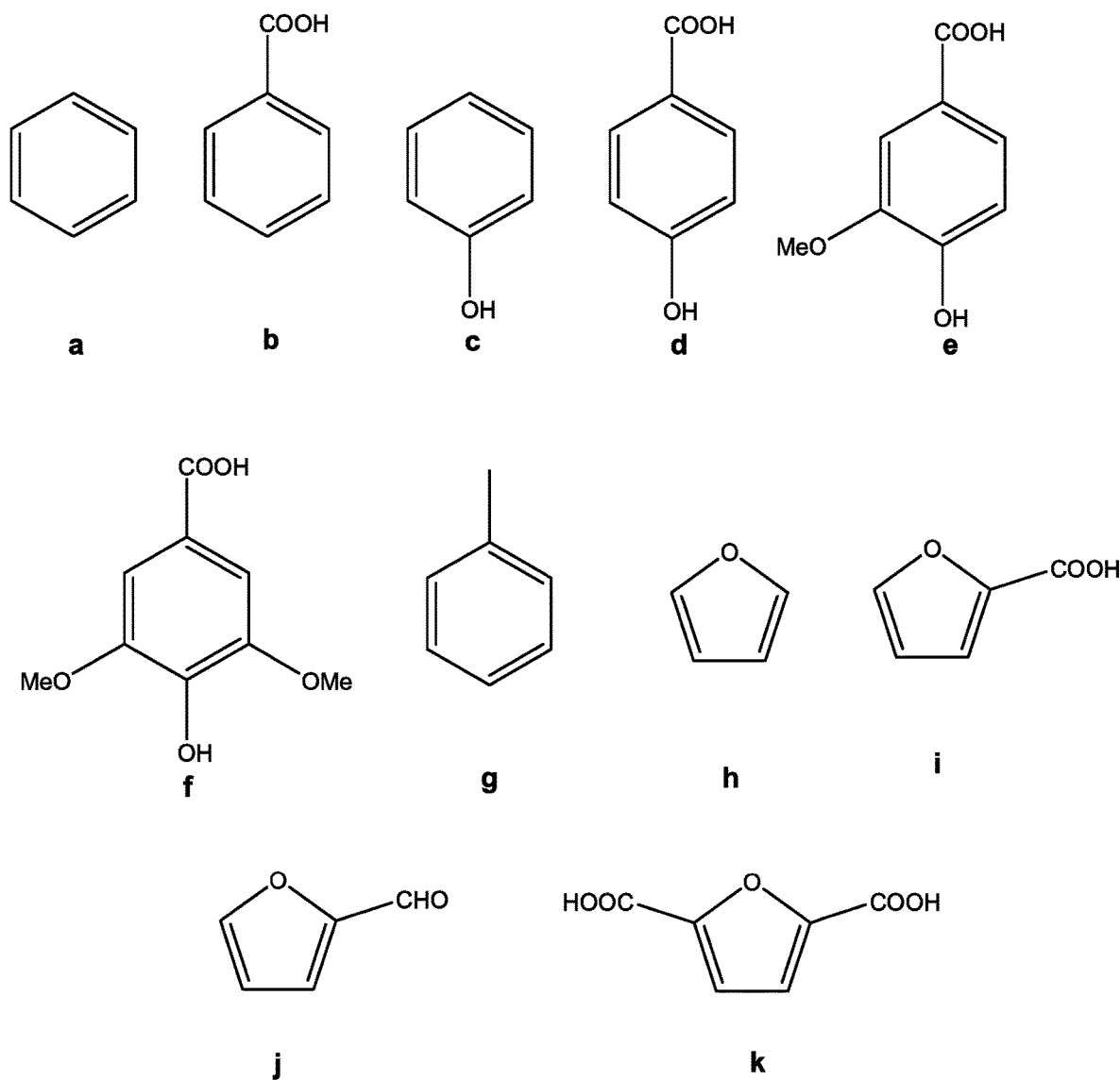
FIG. 8 shows exemplary starting materials for the synthesis of TPA (panels a-g) or FDCA (panels h-j). Panel k shows FDCA.

Furan (FIG. 8, panel h) is a product of the thermal decomposition of pentose-containing materials, such as cellulosic solids like pine-wood. Furfural (FIG. 8, panel j) can form during acid-catalyzed dehydration of C5 sugars such as xylose, which makes up a significant fraction of hemicellulose, a biorenewable resource from plants. Oxidation of furfural can result in furan-2-carboxylic acid, as shown in FIG. 8, panel i. According to the methods of the disclosure, the electrochemical reductive carboxylation of both furan and furan-2-carboxylic acid can lead to the formation of FDCA, as shown in FIG. 8, panel k, in a mechanism analogous to that shown for naphthalene in FIG. 6.

In embodiments wherein the unsaturated organic substrate reactant includes a furan substrate as described above, the dicarboxylic organic product can include furandicarboxylic acid. That is, the dicarboxylic organic product can include, for example, 2,5-furandicarboxylic acid (FDCA) as a product component. Preferably, in these embodiments, the dicarboxylic organic product includes FDCA as substantially the only dicarboxylic organic product isomer.

In embodiments, the unsaturated organic substrate reactant includes a substituted or unsubstituted thiophene. The thiophene substrate can be substituted with up to one carboxylic group, aldehyde group, or hydroxymethyl group. In embodiments wherein the unsaturated organic substrate reactant includes a thiophene substrate as described above, the dicarboxylic organic product can include thiophenedicarboxylic acid. That is, the dicarboxylic organic product can include, for example, 2,5-thiphenedicarboxylic acid as a product component. Preferably, in these embodiments, the dicarboxylic organic product includes 2,5-thiophenedicarboxylic acid as substantially the only dicarboxylic organic product isomer.

In embodiments, the unsaturated organic substrate reactant includes a substituted or unsubstituted pyrrole. The pyrrole substrate can be substituted with up to one carboxylic group, aldehyde group, or hydroxymethyl group. In embodiments wherein the unsaturated organic substrate reactant includes a pyrrole substrate as described above, the dicarboxylic organic product can include pyrroledicarboxylic acid. That is, the dicarboxylic organic product can include, for example, 2,5-pyrroledicarboxylic acid as a product component. Preferably, in these embodiments, the dicarboxylic organic product includes 2,5-pyrroledicarboxylic acid as substantially the only dicarboxylic organic product isomer.

Figure 9:
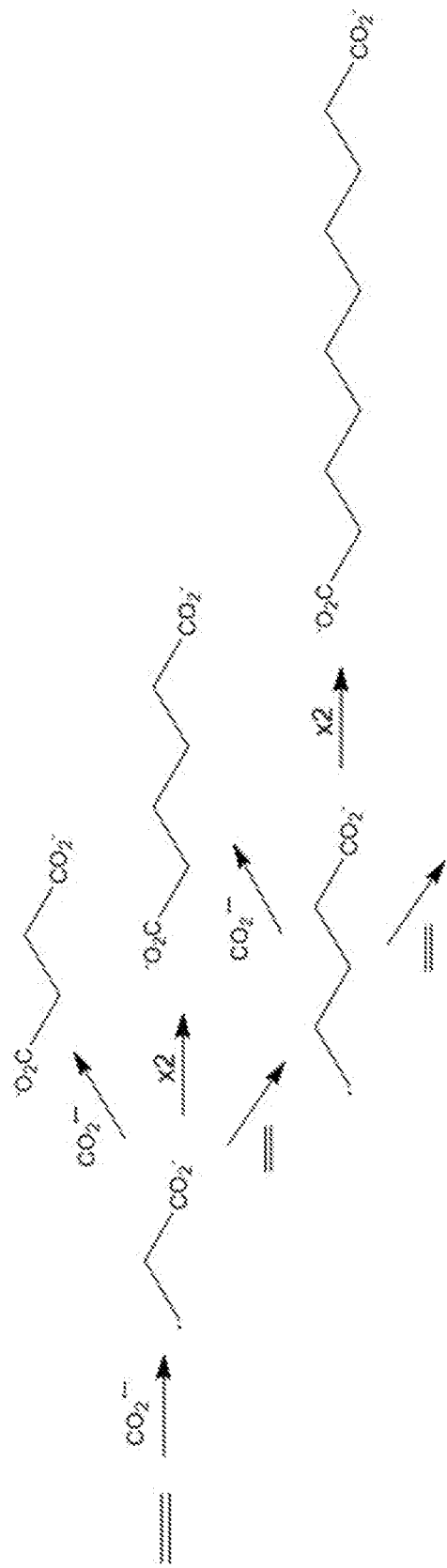
FIG. 9 illustrates the synthesis of adipic acid by electrocarboxylation of ethylene.
Figure 10:
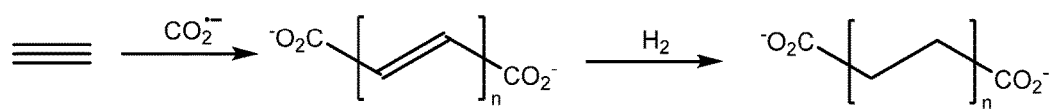
FIG. 10 illustrates the synthesis of adipic acid by electrocarboxylation of acetylene.
Figure 11:
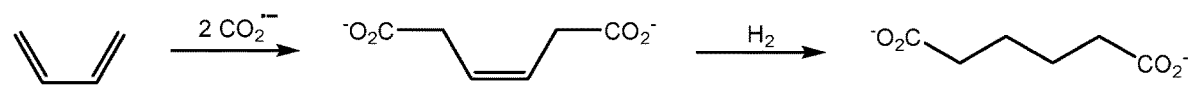
FIG. 11 illustrates the synthesis of adipic acid by electrocarboxylation of 1,3-butadiene.

In embodiments, the unsaturated organic substrate reactant includes one or more of ethylene, acetylene, and 1,3-butanediene. For example, the electrochemical reductive carboxylation of ethylene can proceed through the reactions illustrated in FIG. 9. Advantageously, in contrast with acetylene and butadiene, which are both currently produced from petroleum, ethylene can be produced from renewable ethanol, providing an overall biorenewable process. Similar reactions for the production of adipic acid according to methods of the disclosure wherein the organic substrate reactant is acetylene and 1,3-butanediene are shown in FIGS. 10 and 11, respectively.

In embodiments wherein the unsaturated organic substrate reactant includes one or more of ethylene, acetylene, and 1,3-butanediene, the dicarboxylic organic product includes at least one of adipic acid (AA, 1,6-hexanedioic acid), suberic acid (1,8-octanedioic acid), sebacic acid (1,10-decanedioic acid), and 1,12-dodecandioic acid. The dicarboxylic organic product can result, for example, from the electrocatalytic reduction of an alkylenic hydrocarbon or an alkylynic hydrocarbon, as described above. Optionally, the dicarboxylic organic product can result from an additional, subsequent step-wise oligomerization to form adipic acid or another acid with the desired carbon chain length, and optionally can further include subsequent hydrogenation to remove residual unsaturation.

Supporting Electrolyte

In embodiments, the product medium further includes a supporting electrolyte. The supporting electrolyte can be, for example, a saturated aqueous solution of an inorganic salt or other electrolyte such as potassium bicarbonate. The supporting electrolyte, present in the aqueous phase of the product medium, can suppress the solubility of the organic catholyte components and increase the conductivity of the aqueous phase. Furthermore, the dissolved salts can participate in the chemical reactions resulting in the formation of dicarboxylic acids and their derivatives. In addition, and advantageously, the dissolved electrolyte can reduce the oxygen evolution overvoltage. Suitable examples of cations in the aqueous electrolyte can include, but are not limited to, sodium and/or potassium cations. Suitable examples of anions can include, but are not limited to, formate, oxalate, carbonate, bicarbonate, phosphate, hydrophosphate, dihydrophosphate, borate, or sulfate ions.

Furthermore, in embodiments, the product medium, or the anolyte, is substantially free from the organic liquid. As used herein, "substantially free from the organic liquid" means that the product medium contains less than about 10, less than about 5, less than about 2, less than about 1, or less than about 0.1 wt % of organic liquids in the product medium. The organic liquid can include, for example, any organic solvent, polymer, and/or ionic liquid that may be present in the reactant medium or in the overall reaction system.

Electrochemical Reductive Carboxylation

The methods according to the disclosure include electrochemically reducing the unsaturated organic substrate in the reactant medium with (i) a cathode in the reactant medium and (ii) an anode in the product medium, thereby forming a dicarboxylic organic product corresponding to the unsaturated organic substrate. The reactant medium, unsaturated organic substrate, product medium, and dicarboxylic organic product are as described above. The dicarboxylic organic product is recovered in the product medium, for example after initial formation in the reactant medium and subsequent transport to the product medium based on preferential solubility/miscibility with the product medium.

Electrochemical reduction can include applying a voltage differential or electrical current between the cathode and the anode, such as with a power source in electrical connection with both electrodes.

The reductive carboxylation of the methods disclosed herein can take place via two mechanisms. If the redox potential of the unsaturated organic substrate reactant is more positive than that of a $CO_2/CO_2^-$ couple, the process can proceed through the electron attachment to the organic substrate reactant followed by reaction of the organic substrate reactant radical-anion with carbon dioxide. However, if the electron affinity of $CO_2$ is higher than that of organic substrate reactant, for example in the case of naphthalene, phenanthrene, anthracene, and the like, the reaction can proceed via electron attachment to carbon dioxide, followed by the reaction of the $CO_2^-$ anion-radical with organic substrate reactant molecule.

Any metal or alloy characterized by a high hydrogen evolution overvoltage can be used for the cathode material. Suitable examples of cathode materials include, but are not limited to, at least one of tin, bismuth, gallium, indium, copper, silver, gold, cadmium, mercury, or lead.

Similarly, any metal or alloy capable of withstanding the electrolysis conditions for an extended period of time, and capable of sufficiently reducing the oxygen evolution overvoltage can be used for the anode material. Suitable examples of anode materials include, but are not limited to, nickel, stainless steel, and ruthenium-doped titania. Furthermore, any anode material used for water electrolysis can be used in the processes and methods described herein.

In embodiments, the step of electrochemically reducing the unsaturated organic substrate in the reaction medium, according to the disclosure, can further include forming a formic reaction product. The formic reaction product can be in acid form, such as formic acid (HCOOH), anionic form, such as formate ($HCOO^-$), or salt form, such as metal formate (HCOOM, wherein M can be a metal such as Na, K, other alkali metal, or an organic cation). Similar to the dicarboxylic organic product, the formic reaction product can be initially formed in the reactant medium and subsequently transported to the product medium based on preferential solubility/miscibility with the product medium.

In embodiments, the method can further include electrochemically oxidizing the formic reaction product in the product medium with the anode, thereby forming carbon dioxide as an oxidation product, and recovering the carbon dioxide from the product medium in the reactant medium. The electrochemical oxidation can result from the same voltage differential or electrical current applied between the cathode and the anode for the electrochemical reduction in the reactant medium. Advantageously, the carbon dioxide gas formed in the product medium such as, at the anode, can be transferred back to the reactant medium, for example, as dispersed bubbles buoyantly traveling from the product medium to the reactant medium when the product medium is the denser medium, thus providing a recycle and recovery means of the carbon dioxide reactant that would otherwise be lost or discharged as formic acid waste.

Recovering the Dicarboxylic Organic Product

The method of the disclosure includes recovering the dicarboxylic organic product in the product medium.

The dicarboxylic organic product in the product medium can be recovered by any method known in the art, for example, as a dissolved component in the water of the product medium. For example, the dicarboxylic acid can diffuse from the reactant medium where it is originally formed to the product medium where is it preferentially soluble in the polar aqueous product medium. The dicarboxylic organic product can be subsequently recovered, separated, and isolated from the product medium by any suitable process, such as evaporation, concentration, crystallization, precipitation, and the like.

In embodiments wherein the method includes forming a formic reaction product, as described above, the recovering of the dicarboxylic organic product can further include recovering the formic reaction product in the product medium. For example, analogous to the dicarboxylic organic product, the formic reaction product can be recovered as a dissolved component in the water of the product medium, as the result of the diffusion of the formic reaction product to the product medium from the reaction medium, based on its preferential solubility for the aqueous product medium.

Reaction System

The methods according to the disclosure can generally be batch, semi-batch, or continuous. Providing the reactant medium can include feeding an organic liquid solution already containing the unsaturated organic substrate and carbon dioxide therein to a reaction vessel, feeding unsaturated organic substrate and/or carbon dioxide into an organic liquid medium already in the reaction vessel, continuously feeding organic liquid, unsaturated organic substrate, and carbon dioxide into the reaction vessel, and the like.

In embodiments, the reactant medium and the product medium are in direct liquid-liquid contact.

In embodiments, it can be desirable to perform the methods disclosed herein at elevated pressures to increase the concentration of the dissolved carbon dioxide, resulting in a high rate of $CO_2^-$ generation and, overall, high equipment productivity. It can also be desirable to perform the methods disclosed herein at elevated temperatures to ensure sufficiently high rate of diffusion of the mixture components to each other, reduce the energy loss to the Ohmic heating of the electrolytes, and also reduce the overpotentials due to the water electrooxidation process.

Figure 12:
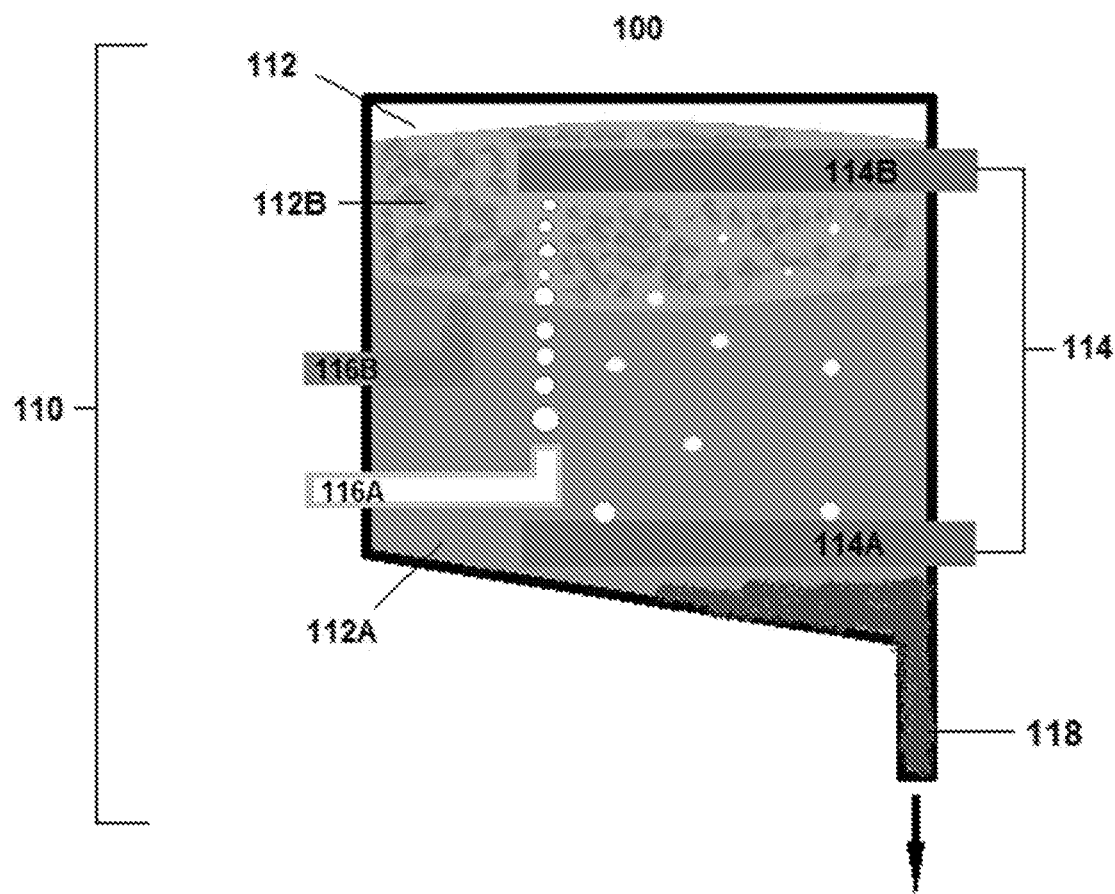
FIG. 12 illustrates an exemplary reaction vessel according to the disclosure.

The disclosure further provides a reaction system 100 for electrochemical carboxylation of an unsaturated organic substrate, for example as illustrated in FIG. 12. The reaction system can include a reaction vessel 110 having an interior volume 112 and defining a product region 112A in the interior volume 112 and a reactant region 112B in the interior volume 112. The reaction system 100 can further include an anode 114A positioned in the product region 112A, and a cathode 114B positioned in the reactant region 112B, and an electrical power source 114 in electrical contact with the cathode 114B and the anode 114A. The reaction system 100 further includes a source 116B of reactant medium components (e.g., one or more of organic liquid for reactant medium, organic substrate reactant, supporting electrolyte) in fluid communication with the reactant region 112B of the reaction vessel 110, the reaction medium as described herein, and a source 116A of carbon dioxide reactant in fluid communication with the reactant region 112B. As illustrated, the sources 116A, 116B can be physically located in the product region 112A, with buoyancy effects causing transport of the introduced materials to the reactant region 112B (e.g., as dispersed gas-phase bubbles or lower-density bubbles). In other embodiments, one or both of the sources 116A, 116B can be physically located in the reactant region 112B for direct introduction therein. Additionally, the reaction system 100 can include a source (not shown) of product medium components (e.g., one or more of water, electrolytes) in fluid communication with the product region 112A of the reaction vessel 110, the product medium including water, as described herein. The various sources of reactant medium components, carbon dioxide reactant, product medium components, etc. can include tubes, pipes, or other delivery conduits for their respective materials, for example to initially charge the reaction vessel 110 with one or more reaction components, to provide a continuous flow or supply of one or more reaction components, and/or to provide a make-up flow or supply of one or more reaction components. The reaction vessel 110 can further include an outlet or drain 118, for example positioned at or near the base of the vessel 110 in the product region 112A, which in turn can be used for final product recovery or removal from the vessel 110. For example, a relatively more water-soluble dicarboxylic organic product in anionic form (—COO$^-$) and/or salt form (—COOM) can be protonated in the product region 112A to form a relatively less water-soluble (or insoluble) corresponding dicarboxylic organic product in acid form (—COOH), which can be recovered as a precipitate via the outlet 118.

In general, the reactant region 112B and corresponding reactant medium can be positioned above the product region 112A and corresponding product medium, relative to the direction of gravity, for normal operation of the reaction vessel 110. The cathode 114B can be positioned and/or adapted to contact the reactant medium when the reactant medium is present in the reaction vessel 110, and the anode 114A can be positioned and/or adapted to contact the product medium when the product medium is present in the reaction vessel 110. The electrical power source 114 can be external to the reaction vessel and adapted to apply a voltage or electrical current between the anode 114A and the cathode 114B. The source of the reactant medium and/or the product medium can be a single source or inlet of the corresponding medium as a mixture, or it can be multiple sources or inlets to feed the corresponding medium separately or in subcombination for mixing of the reaction and product medium in their respective regions of the reaction vessel. The reaction system 100 can be used to perform the methods disclosed herein for the electrochemical reductive carboxylation of an unsaturated organic substrate in any of the various disclosed embodiments and refinements.

Figure 13:
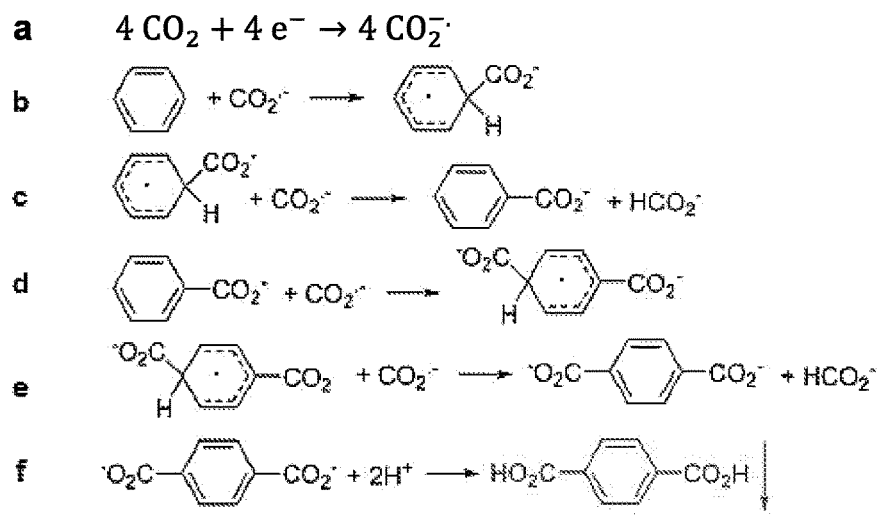
FIG. 13, panels a-f, show an exemplary electrochemical reductive carboxylation process of benzene according to methods of the disclosure.

FIG. 13 illustrates an exemplary electrochemical reductive carboxylation pathway of benzene into terephthalic acid in a reaction vessel according to the disclosure, such as the reaction vessel 110 illustrated in FIG. 12. FIG. 13, panel a shows the electroreduction of $CO_2$ that takes place at the cathode 114B surface, while panels b-e illustrate the reactions that occur in the cathode region, that is homogeneously within the reactant medium in reactant region 112B. The terephthalic anions, generated as shown in panel e, do not react with the $CO_2^-$ radical anions due to Coulombic repulsion and low efficiency of the charge screening in the reactant medium. After diffusion of the TPA anions to the aqueous phase, that is the product region 112A, the TPA anions undergo protonation into TPA, shown in FIG. 13, panel f, which precipitates and can be recovered via the outlet 118. The formate ions generated as shown in FIG. 13 panels c and e can migrate through the product medium to the anode 114A, where they are oxidized into carbon dioxide, which can bubble up through the product medium to the reactant medium to be recycled and reused in the electrocarboxylation of benzene.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compounds, compositions, methods, and processes are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

EXAMPLES

Example 1—Formation of Naphthalenecarboxylic Acids

To verify the formation of carboxylic acids by the reaction of aromatic radical anions with carbon dioxide, a solution of sodium naphthalide was prepared by stirring metallic sodium in THF solution with naphthalene overnight. Subsequently, dry carbon dioxide was passed over the dark-green solution upon stirring until the color disappeared. The solution was then quenched with water, acidified with hydrochloric acid, and the organic products were analyzed by $^1$H and $^{13}$C NMR, as well as mass spectrometry (MS).

The NMR and mass spectra (not shown) indicated that naphthalene constituted approximately 50% of the resulting aromatic compounds, on a molar basis. The numerous peaks at 6.8-7.4 ppm in the $^1$H NMR spectrum were consistent with the formation of numerous aromatic products. Peaks at 5.8-6.6 ppm were consistent with the formation of vinyl protons on a partially reduced aromatic ring. Significantly, the broad peak at 9.1-9.7 ppm was consistent with the carboxylic proton —COOH, and demonstrates the reductive carboxylation of the naphthalene. The carboxylate peak area was about 2.68, with a total area under naphthalene peaks of about 8.

In the $^{13}$C NMR spectrum, the peaks with chemical shifts of 173.659 and 177.135 ppm, and smaller peaks in the 164-180 ppm region were consistent with the formation of new carboxylate groups.

The mass spectrum had characteristic peaks at m/z of 171, 173, 175, 217, 219, and 263, indicative of the fragments as shown in Table 1, below, which are consistent with the formation of carboxylic acids from naphthalene reduction, followed by carbon dioxide treatment. The substances with higher molecular mass likely resulted from the coupling of naphthalene radicals.

| M/z Value | Corresponding Fragment |
|---|---|
| 171 | $C_{10}H_7^+$—COOH |
| 173 | $C_{10}H_8COOH \cdot H^+$ |
| 175 | $C_{10}H_{10}COOH \cdot H^+$ |
| 217 | $C_{10}H_6(COOH)_2 \cdot H^+$ |
| 219 | $C_{10}H_8(COOH)_2 \cdot H^+$ |
| 263 | $C_{10}H_7(COOH)_3 \cdot H^+$ |

Therefore, Example 1 demonstrates the formation of naphthalenecarboxylic acids by reductive carboxylation. Similar compounds can be obtained in the course of electrochemical carboxylation of naphthalene, as well as other unsaturated compounds, such as benzene.

Example 2—Synthesis of Sodium Salt of Anthraquinonedicarboxylic Acid

Figure 14:
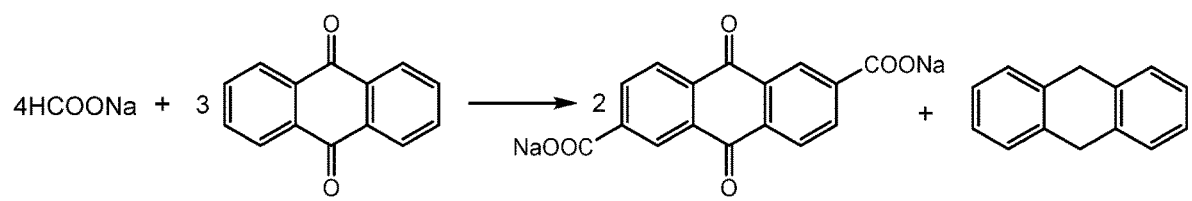
FIG. 14 illustrates the reaction of anthraquinone with HCOONa and the corresponding reaction products.

Joint thermolysis of 9,10-anthraquinone as an unsaturated organic substrate reactant and HCOONa as a carbon dioxide reactant (e.g., a source of formate groups for in situ formation of carbon dioxide or carboxylate ions) at 350° C. was performed in a glycerine solution. A small fraction of anthraquinone was converted into 9,10-dihydroanthraqunione based on NMR and MS analysis. However, the majority of the anthraquinone was successfully converted into a glycerine- and water-soluble product, identified as the sodium salt of anthraquinonedicarboxylic acid, as illustrated in FIG. 14. Furthermore, the absence of gas evolution, as would be expected from the oxidation of HCOONa by anthraquinone, is consistent with the carbon dioxide moieties attaching to the anthraquinone aromatic nuclei instead of evolving as carbon dioxide gas.

Accordingly, Example 2 demonstrates the successful synthesis of a salt of anthraquinonedicarboxylic acid according to the methods of the disclosure.

REFERENCES

1. Synthesis methods for 2,6-naphthalenedicarboxylic acid. A. R. Elman. Catalysis in Industry. Catalysis in Chemical and Petrochemical Industry. September 2009, 1, 184. DOI: 10.1134/S2070050409030039.
2. The electrochemical characteristics of cathodic processes involving aromatic hydrocarbons and carbon dioxide. Part I. General mechanistic considerations. Ticianelli, E. A.; Avaca, L. A.; Gonzalez, E. R. *Journal of Electroanalytical Chemistry and Interfacial Electrochemistry* (1989), 258 (2), 369-77.
3. The electrochemical characteristics of cathodic processes involving aromatic hydrocarbons and carbon dioxide. Part II. The ECE/DISP problem. Ticianelli, E. A.; Avaca, L. A.; Gonzalez, E. R. *Journal of Electroanalytical Chemistry and Interfacial Electrochemistry* (1989), 258(2), 379-89.
4. Electrolytic reduction of phenanthrene. Hu, Ming; Liu, Xuguang; Wang, Zhizhong. *Ranliao Huaxue Xuebao* (1994), 22(2), 219-23.
5. Electrochemical reduction of polyaromatic compounds. Gagyi Palffy, E.; Starzewski, P.; Labani, A.; Fontana, A. *Journal of Applied Electrochemistry* (1994), 24(4), 337-43.
6. Electrochemical hydrogenation and hydrogenolysis in aqueous media: final report. Kariv-Miller, E. Report (1989), (DOE/PC/70807-T1; Order No. DE91005742), 16 pp.
7. Electroreduction in aqueous media, saturation of polycyclic aromatics. Kariv-Miller, E.; Pacut, R. I. Report (1986), (DOE/PC/70754-T2; Order No. DE86006973), 11 pp.
8. Electroreduction in aqueous media. Saturation of polycyclic aromatics. Kariv-Miller, Essie; Pacut, Ryszard I. *Tetrahedron* (1986), 42(8), 2185-92.
9. Study of the electrochemical reduction of aromatic polynuclear hydrocarbons in dimethylacetamide. Breant, M.; Georges, J. *Analytica Chimica Acta* (1977), 90(1), 111-18.
10. The electrochemical reduction of a low-volatile bituminous coal; nature of the reduced material. Sternberg, Heinz W.; Delle Donne, Charles L.; Markby, Raymond E.; Wender, Irving. *Fuel* (1966), 45(6), 469-82.
11. Electrocatalytic upgrading of model lignin monomers with earth abundant metal. Lam, Chun Ho; Lowe, Christy B.; Li, Zhenglong; Longe, Kelsey N.; Rayburn, Jordan T.; Caldwell, Michael A.; Houdek, Carly E.; Maguire, Jack B.; Saffron, Christopher M.; Miller, Dennis J.; et al. *Green Chemistry* (2015), 17(1), 601-609.
12. The Birch reduction of aromatic compounds. Rabideau, Peter W. and Marcinow, Zbigniew. *Organic Reactions* (Hoboken, NJ, United States), 42, 1992.

13. J. A. Rosso et al. *J. Phys. Org. Chem.* 2001; 14: 300-309. D01:10.1002/poc.365

14. Mechanism of the thermal decomposition of oxalates. Boldyrev, V. V.; Nev'yantsev, 1. S.; Mikhailov, Yu. I.; Khairetdinov, E. F. *Kinetika i Kataliz* (1970), 11(2), 367-73.

What is claimed is:

1. A method for electrochemical reductive carboxylation of an unsaturated organic substrate, the method comprising:
   (a) providing a reactant medium comprising a water-immiscible, ionically conductive, aprotic organic liquid comprising an ionic liquid comprising one or more ionic liquid cations and one or more ionic liquid counter anions, an unsaturated organic substrate reactant, and a carbon dioxide reactant, wherein the reactant medium is free from cation electrolytes other than the one or more ionic liquid cations;
   (b) providing a product medium comprising water;
   (c) electrochemically reducing the unsaturated organic substrate reactant in the reactant medium with (i) a cathode in the reactant medium and (ii) an anode in the product medium, thereby forming a dicarboxylic organic product comprising a reaction product between (i) at least one of the unsaturated organic substrate reactant and a radical-anion of the unsaturated organic substrate reactant, and (ii) at least one of carboanions formed from the carbon dioxide reactant, $CO_2^-$ anion-radicals formed from the carbon dioxide reactant, and the carbon dioxide reactant in the reactant medium; and
   (d) recovering the dicarboxylic organic product in the product medium after transport of the dicarboxylic organic product formed in the reactant medium to the product medium.

2. The method of claim 1, wherein the one or more ionic liquid cations are selected from the group consisting of substituted ammonium cations, substituted phosphonium ions, substituted sulfonium ions, substituted aromatic heterocyclic rings having at least one quaternary ammonium cation, and combinations thereof.

3. The method of claim 1, wherein the unsaturated organic substrate reactant comprises at least one of an aromatic hydrocarbon substrate, a heteroaromatic hydrocarbon substrate, an alkylenic hydrocarbon substrate, and an alkylynic hydrocarbon substrate.

4. The method of claim 3, wherein:
   the unsaturated organic substrate reactant comprises a substituted or unsubstituted naphthalene; and
   the dicarboxylic organic product comprises naphthalenedicarboxylic acid.

5. The method of claim 3, wherein:
   the unsaturated organic substrate reactant comprises a substituted or unsubstituted furan; and
   the dicarboxylic organic product comprises furandicarboxylic acid.

6. The method of claim 3, wherein:
   the unsaturated organic substrate reactant comprises a substituted or unsubstituted thiophene; and
   the dicarboxylic organic product comprises a thiophenedicarboxylic acid.

7. The method of claim 3, wherein:
   the unsaturated organic substrate reactant comprises a substituted or unsubstituted pyrrole; and
   the dicarboxylic organic product comprises a pyrroledicarboxylic acid.

8. The method of claim 3, wherein:
   the unsaturated organic substrate reactant comprises one or more of ethylene, acetylene, and 1,3-butadiene; and
   the dicarboxylic organic product comprises at least one of adipic acid, suberic acid, sebacic acid, and 1,12-dodecanedioic acid.

9. The method of claim 3, wherein:
   the unsaturated organic substrate reactant comprises a substituted or unsubstituted benzene; and
   the dicarboxylic organic product comprises phthalic acid.

10. The method of claim 1, wherein electrochemically reducing the unsaturated organic substrate reactant in the reactant medium in part (c) further comprises forming a formic reaction product.

11. The method of claim 10, wherein:
    recovering the dicarboxylic organic product in part (d) further comprises recovering the formic reaction product in the product medium.

12. The method of claim 11, further comprising:
    electrochemically oxidizing the formic reaction product recovered in the product medium with the anode, thereby forming carbon dioxide as an oxidation product in the product medium; and
    recovering the carbon dioxide from the reactant medium, after buoyant transport of the carbon dioxide formed in the product medium to the reactant medium.

13. The method of claim 1, wherein the reactant medium and the product medium are in direct liquid-liquid contact.

14. The method of claim 1, wherein the reactant medium is substantially free from water.

15. The method of claim 1, wherein the product medium further comprises a supporting electrolyte.

16. The method of claim 1, wherein:
    the cathode comprises at least one of tin, bismuth, gallium, indium, copper, silver, gold, cadmium, mercury, and lead; and
    the anode comprises at least one of nickel, stainless steel, and ruthenium-doped titania.

17. The method of claim 1, wherein electrochemically reducing the unsaturated organic substrate reactant comprises forming a $CO_2^-$ anion-radical from the carbon dioxide reactant, and then subsequently reacting the $CO_2^-$ anion-radical with the unsaturated organic substrate reactant.

18. The method of claim 1, wherein the dicarboxylic organic product is preferentially soluble in the product medium as compared to the reaction medium.

19. The method of claim 1, wherein the unsaturated organic substrate reactant comprises an aromatic hydrocarbon substrate.

* * * * *